(12) United States Patent
Kimura et al.

(10) Patent No.: US 8,095,330 B2
(45) Date of Patent: Jan. 10, 2012

(54) POSITION DETECTING DEVICE

(75) Inventors: Atsushi Kimura, Akiruno (JP); Akio Uchiyama, Yokohama (JP); Atsushi Chiba, Hachioji (JP); Ryoji Sato, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 22 days.

(21) Appl. No.: 12/729,370

(22) Filed: Mar. 23, 2010

(65) Prior Publication Data
US 2010/0179782 A1 Jul. 15, 2010

Related U.S. Application Data

(63) Continuation of application No. PCT/JP2008/067330, filed on Sep. 25, 2008.

(30) Foreign Application Priority Data

Sep. 25, 2007 (JP) ................................ 2007-247922

(51) Int. Cl.
*G06F 19/00* (2006.01)
*A61B 5/05* (2006.01)

(52) U.S. Cl. .......................................... 702/94; 600/424
(58) Field of Classification Search .................... 702/94, 702/150, 152; 382/154, 285; 600/424
See application file for complete search history.

(56) References Cited

U.S. PATENT DOCUMENTS

| | | |
|---|---|---|
| 5,594,849 A | 1/1997 | Kuc et al. |
| 2005/0216231 A1 | 9/2005 | Aoki et al. |
| 2008/0177177 A1 | 7/2008 | Aoki et al. |
| 2008/0177178 A1 | 7/2008 | Aoki et al. |
| 2008/0281188 A1 | 11/2008 | Aoki et al. |
| 2009/0022369 A1 * | 1/2009 | Satoh et al. .................... 382/106 |

FOREIGN PATENT DOCUMENTS

| | | |
|---|---|---|
| JP | 5-197767 | 8/1993 |
| JP | 8-98824 | 4/1996 |
| JP | 8-103420 | 4/1996 |
| JP | 2000-337811 | 12/2000 |
| JP | 2001-179700 | 7/2001 |
| JP | 2002-186675 | 7/2002 |
| JP | 2004-295443 | 10/2004 |
| WO | WO 2005/112733 A1 | 12/2005 |

* cited by examiner

*Primary Examiner* — Bryan Bui
(74) *Attorney, Agent, or Firm* — Scully, Scott, Murphy & Presser, P.C.

(57) ABSTRACT

A position detecting device includes a position calculator that performs an optimization convergence calculation using an evaluation function that expresses an error between a measurement value and a theoretical value of magnetic field information of a detection target to calculate at least a position of the detection target; a storage unit that stores a final convergence result of the optimization convergence calculation performed by the position calculator; and a controller that determines whether a result of the optimization convergence calculation converges, suspends the optimization convergence calculation performed by the position calculator when the result does not converge, and performs, after a predetermined time has passed, a returning process of returning a state of the optimization convergence calculation to a converged state by causing the position calculator to perform the optimization convergence calculation based on the final convergence result.

18 Claims, 11 Drawing Sheets

POSITION DETECTING DEVICE

CROSS-REFERENCE TO RELATED APPLICATIONS

This application is a continuation of PCT international application Ser. No. PCT/JP2008/067330 filed on Sep. 25, 2008 which designates the United States, incorporated herein by reference, and which claims the benefit of priority from Japanese Patent Application No. 2007-247922, filed on Sep. 25, 2007, incorporated herein by reference.

BACKGROUND OF THE INVENTION

1. Field of the Invention

The present invention relates to a position detecting device that detects a position of a detection target based on a detection result of a magnetic field emitted from the detection target.

2. Description of the Related Art

In the technical field of endoscope, a capsule endoscope that can be introduced into a digestive canal of a subject, such as a patient, has conventionally been developed. The capsule endoscope is swallowed from a mouth of the subject to acquire images (hereinafter, occasionally referred to as "in-vivo images") inside internal organs of the subject while moving in the digestive canal with peristaltic movements, and wirelessly transmits acquired in-vivo images to a receiving device located outside the subject. The capsule endoscope sequentially acquires in-vivo images of the subject since it is introduced into the digestive canal of the subject until it is naturally excreted from the subject.

Furthermore, a system that guides (that is, magnetically guides) a capsule endoscope introduced into a subject by a magnetic force has been proposed (see, for example, International Publication No. WO2005/112733 Pamphlet). In this system, an LC resonance circuit (hereinafter, "LC marker"), which uses a coil and a capacitor, and a magnet are incorporated in the capsule endoscope. The position of the capsule endoscope is detected based on a detection result of an induced magnetic field emitted from the LC marker. The magnetic field formed at the detected position is caused to act on the magnet in the capsule endoscope, thereby magnetically guiding the capsule endoscope in the subject.

A position detecting device that detects the position of a capsule endoscope generally detects, using a plurality of detection coils, an induced magnetic field emitted from an LC marker in the capsule endoscope due to application of an external magnetic field. The position detecting device calculates the position of the capsule endoscope based on a detection result of the induced magnetic field. The position detecting device sets an evaluation function that expresses an error between a field-strength detection value (a measurement value) of each detection coil and a field-strength theoretical value of each detection coil. This field-strength theoretical value is a field-strength value of an induced magnetic field theoretically detected by each detection coil from the LC marker in the capsule endoscope that is in a state of being directed to a provisional direction at a provisional position. The theoretical value is calculated in accordance with a predetermined operation expression. The position detecting device performs optimization convergence calculations based on such an evaluation function to calculate the provisional position and the provisional direction as the position information and direction information of the capsule endoscope. The provisional position and the provisional direction are values at which an error value in the optimization convergence calculation becomes equal to or less than a predetermined threshold (that is, converges). Such a position detecting device repeatedly performs the optimization convergence calculation by using a result of optimization convergence calculation, which is obtained when the error value in the optimization convergence calculation converges to a value equal to or less than a predetermined threshold, as a starting point of calculation for the next optimization convergence calculation. The position detecting device sequentially calculates the position information and direction information of the capsule endoscope.

SUMMARY OF THE INVENTION

A position detecting device according to an aspect of the present invention includes a position calculator that performs an optimization convergence calculation using an evaluation function that expresses an error between a measurement value and a theoretical value of magnetic field information of a detection target to calculate at least a position of the detection target; a storage unit that stores a final convergence result of the optimization convergence calculation performed by the position calculator; and a controller that determines whether a result of the optimization convergence calculation converges, suspends the optimization convergence calculation performed by the position calculator when the result does not converge, and performs, after a predetermined time has passed, a returning process of returning a state of the optimization convergence calculation to a converged state by causing the position calculator to perform the optimization convergence calculation based on the final convergence result.

A position detecting device according to another aspect of the present invention includes a position calculator that performs an optimization convergence calculation using an evaluation function that expresses an error between a measurement value and a theoretical value of magnetic field information of a detection target to calculate at least a position of the detection target; a threshold storage unit that stores a threshold concerning a measurement value of the magnetic field information; and a controller that compares the measurement value of the magnetic field information with the threshold to determine a difference between the measurement value of the magnetic field information and the threshold, permits, when the measurement value of the magnetic field information is equal to or larger than the threshold, the optimization convergence calculation performed by the position calculator, and prohibits, when the measurement value of the magnetic field information is smaller than the threshold, the optimization convergence calculation performed by the position calculator.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A position detecting device, which is the best mode for carrying out the present invention, is explained below. A position detecting device used for a capsule guiding system that magnetically guides a capsule endoscope (an example of a capsule medical device) that captures in-vivo images of a subject is exemplified as an example of a position detecting device according to the present invention. However, the present invention is not limited to this embodiment.

First Embodiment

Figure 1:
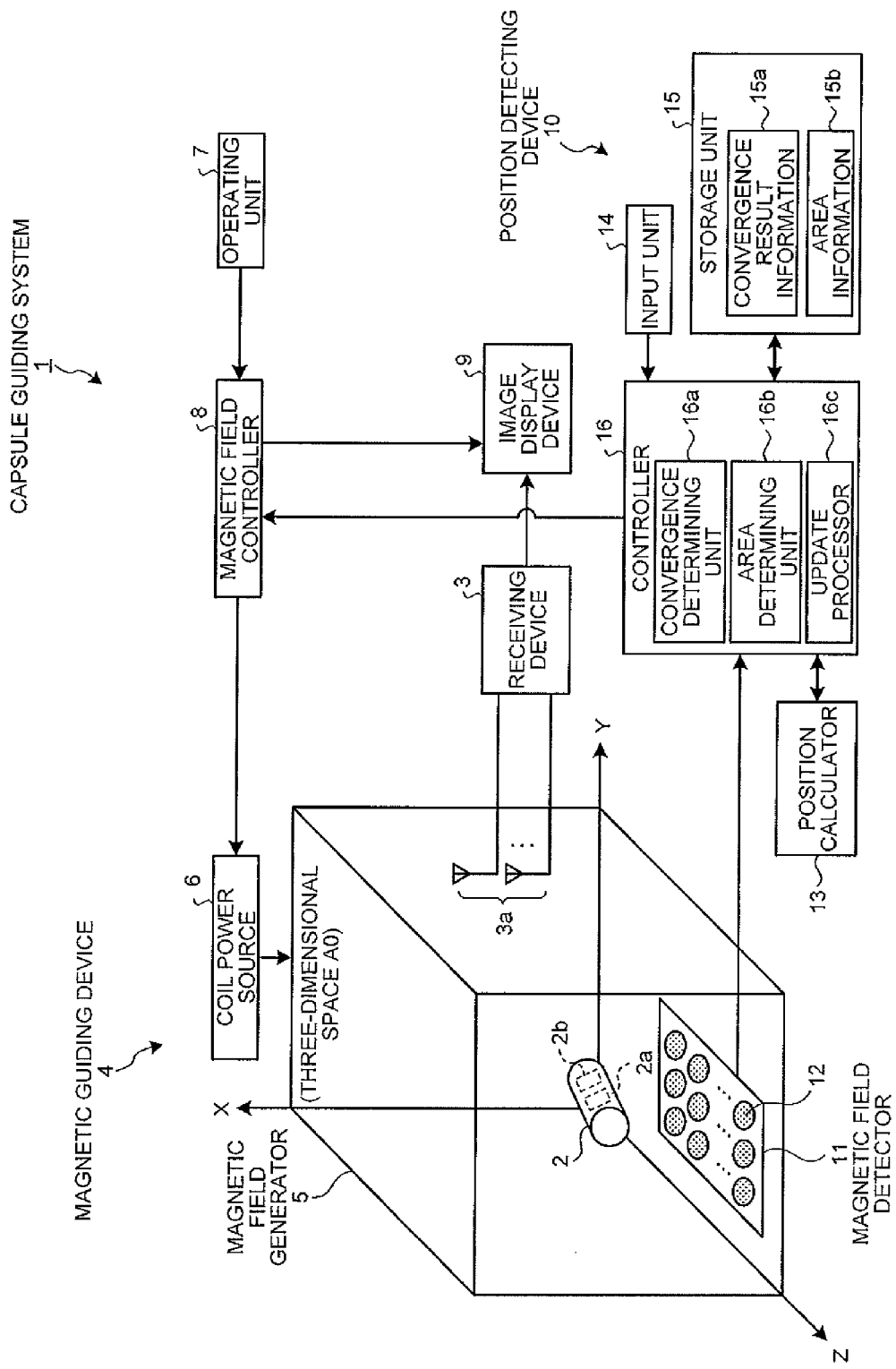
FIG. 1 is a block diagram schematically depicting a configuration example of a capsule guiding system according to a first embodiment of the present invention.

FIG. 1 is a block diagram schematically depicting a configuration example of a capsule guiding system 1 according to a first embodiment of the present invention. As shown in FIG. 1, the capsule guiding system 1 according to the first embodiment includes a capsule endoscope 2 that captures in-vivo images of a subject, a receiving device 3 that receives the in-vivo images from the capsule endoscope 2, a magnetic guiding device 4 that magnetically guides the capsule endoscope 2 introduced into the subject, an image display device 9 that displays the in-vivo images and the like captured by the capsule endoscope 2 in the subject, and a position detecting device 10 that detects position and direction of the capsule endoscope 2 in the subject.

The capsule endoscope 2 is an example of a detection target whose position and direction are detected by the position detecting device 10, and is a capsule medical device that acquires an in-vivo image of the subject. Specifically, the capsule endoscope 2 has an imaging function and a wireless communication function in a capsule-shaped casing, and is introduced in the digestive canal of a subject (not shown) such as a patient. The capsule endoscope 2 sequentially captures in-vivo images while moving in the digestive canal of the subject, and wirelessly transmits image signals including acquired in-vivo images sequentially to the receiving device 3 outside the subject. The capsule endoscope 2 includes in the capsule-shaped casing a magnet $2a$ for enabling magnetic guidance by the magnetic guiding device 4, and a magnetic field generator $2b$ that generates a magnetic field to be used for a detecting process of a position and direction by the position detecting device 10. The magnet $2a$ is realized by a magnetic body such as a permanent magnet or an electromagnet, and moves following the magnetic field formed by the magnetic guiding device 4. The capsule endoscope 2 moves due to an action of the magnet $2a$. As a result, the capsule endoscope 2 is magnetically guided by the magnetic guiding device 4. The magnetic field generator $2b$ is realized by using a coil or the like, and generates the magnetic field outside the capsule endoscope 2. The magnetic field generated by the magnetic field generator $2b$ is detected by a magnetic field detector 11 in the position detecting device 10 described later.

The receiving device 3 has a plurality of receiving antennas $3a$ to receive the in-vivo images of the subject from the capsule endoscope 2 via the receiving antenna $3a$. Specifically, the receiving antennas $3a$ are distributed and arranged on a body surface of the subject, into the digestive canal of which the capsule endoscope 2 is introduced, to capture a radio signal from the capsule endoscope 2 moving (or magnetically guided) along the digestive canal. The receiving device 3 receives the radio signal from the capsule endoscope 2 via the receiving antenna $3a$ to perform a predetermined demodulation process with respect to the received radio signal, and extracts an image signal included in the radio signal. The image signal extracted by the receiving device 3 includes the in-vivo image captured by the capsule endoscope 2. The receiving device 3 transmits the image signal of the in-vivo image to the image display device 9.

The magnetic guiding device 4 magnetically guides the capsule endoscope 2 and includes a magnetic field generator 5 that generates the magnetic field for guiding the capsule endoscope 2 in the subject, a coil power source 6 that supplies electric current to a coil (an electromagnet) of the magnetic field generator 5, an operating unit 7 that operates magnetic guidance of the capsule endoscope 2, and a magnetic field controller 8 that controls strength and direction of the magnetic field generated by the magnetic field generator 5.

The magnetic field generator 5 is realized by combining a plurality of electromagnets such as a Helmholtz coil, to generate a magnetic field capable of guiding the capsule endoscope 2 in the subject. Specifically, in the magnetic field generator 5, a three-axis orthogonal coordinate system (hereinafter, "absolute coordinate system") formed of orthogonal three axes (X-axis, Y-axis, and Z-axis) is defined, to generate a magnetic field of a desired strength, respectively, in respective axial directions (X-axis direction, Y-axis direction, and Z-axis direction) of the absolute coordinate system. The magnetic field generator 5 forms a three-dimensional magnetic field formed by the magnetic field in the respective axial directions of the absolute coordinate system inside a three-dimensional space A0 of the absolute coordinate system (that is, inside a space surrounded by the electromagnets in the magnetic field generator 5), and applies the magnetic field to the magnet $2a$ in the capsule endoscope 2 positioned in the subject (not shown) on a bed, which has moved into the three-dimensional space A0. The magnetic field generator 5 magnetically guides the capsule endoscope 2 by the magnetic field. The magnetic fields in the respective axial directions of the absolute coordinate system generated by the magnetic field generator 5 (that is, rotating magnetic field and gradient magnetic field) are controlled by the current supplied from the coil power source 6 (an energization amount from the coil power source 6).

As described above, the absolute coordinate system can be the three-axis orthogonal coordinate system defined with respect to the magnetic field generator 5 (that is, fixed to the magnetic field generator 5); however, the absolute coordinate system can be a three-axis orthogonal coordinate system fixed to the subject (not shown) incorporating the capsule endoscope 2 in the digestive canal, or a three-axis orthogonal coordinate system fixed to a bed (not shown) on which the subject lies.

The coil power source 6 supplies the current for generating the magnetic field that realizes the magnetic guidance of the capsule endoscope 2 in the subject to the magnetic field generator 5. The coil power source 6 has a plurality of power sources corresponding to a plurality of coils (not shown) forming the magnetic field generator 5, and respectively supplies alternating current to the coils in the magnetic field generator 5 under control of the magnetic field controller 8, to generate the magnetic fields in the respective axial directions of the absolute coordinate system.

The operating unit 7 is realized by using an input device such as a lever and an input button. The operating unit 7 inputs instruction information for instructing the magnetic guidance of the capsule endoscope 2 to the magnetic field controller 8 in response to an input operation by a user such as a doctor or nurse.

The magnetic field controller 8 controls the energization amount of the coil power source 6 with respect to the magnetic field generator 5 based on the instruction information input by the operating unit 7, and controls a magnetic-field generation operation of the magnetic field generator 5 that generates the three-dimensional magnetic field under control of the coil power source 6. In this case, the magnetic field controller 8 acquires position and direction information including respective pieces of information of current position and current direction of the capsule endoscope 2 in the subject from a controller 16 of the position detecting device 10 described later, and determines the strength and direction of the magnetic field to be applied to the capsule endoscope 2 based on the acquired position and direction information. The magnetic field controller 8 causes the magnetic field generator 5 to generate the magnetic field having strength and direction for realizing the magnetic guidance of the capsule endoscope 2 instructed by the instruction information from the operating unit 7, at a current position of the capsule endoscope 2 in the subject. As a result, the magnetic field controller 8 controls the magnetic guidance of the capsule endoscope 2 at a desired position or in a desired direction in the subject.

The magnetic field controller 8 stores the strength and direction of the magnetic field applied to the capsule endoscope 2 in the three-dimensional space A0 (specifically, in the subject) by the magnetic field generator 5 at the time of controlling the magnetic guidance of the capsule endoscope 2 as field strength information and field direction information. When transmission is instructed from the image display device 9, the magnetic field controller 8 transmits the field strength information, the field direction information, and the position and direction information acquired from the position detecting device 10 to the image display device 9.

The image display device 9 displays various pieces of information such as in-vivo images of a subject captured by the capsule endoscope 2, and has a configuration of a workstation or the like that fetches various pieces of information from the receiving device 3 and the magnetic guiding device 4, and stores and displays the fetched various pieces of information. Specifically, the image display device 9 fetches in-vivo images and the like of the subject from the receiving device 3, and fetches the field strength information, the field direction information, and the position and direction information from the magnetic field controller 8. The image display device 9 displays the various pieces of information such as in-vivo images, field strength information, field direction information, and position and direction information on a screen. The user such as a doctor or nurse checks the various pieces of information displayed by the image display device 9 to observe inside of the organs of the subject and performs the magnetically guiding operation of the capsule endoscope 2 using the operating unit 7.

The position detecting device 10 detects the position and direction of the capsule endoscope 2 in the subject positioned in the three-dimensional space A0 of the absolute coordinate system. The position detecting device 10 includes the magnetic field detector 11 that detects the magnetic field emitted from the capsule endoscope 2, a position calculator 13 that calculates the position and direction of the capsule endoscope 2 based on a magnetic-field detection result by the magnetic field detector 11, an input unit 14 that input various pieces of information, a storage unit 15 that stores various pieces of information, and the controller 16 that controls respective components of the position detecting device 10.

The magnetic field detector 11 has a plurality of detection coils 12 to detect the magnetic field generated by the magnetic field generator 2b incorporated in the capsule endoscope 2. Specifically, the detection coils 12 are arranged, for example, in a matrix, and convert the magnetic field from the magnetic field generator 2b (an alternating magnetic field) to a voltage and respectively detect the voltage. The magnetic field detector 11 performs predetermined arithmetic processing using voltage detection values $Vd_1, \ldots, Vd_n$ (n is the number of arranged detection coils 12) of the respective detection coils 12 and a proportionality coefficient, thereby acquiring field-strength detection values $Bd_1, \ldots, Bd_n$, which are measurement values of the field strength acquired by the respective detection coils 12. The magnetic field detector 11 transmits the field-strength detection values $Bd_1, \ldots, Bd_n$ as a magnetic-field detection result of the respective detection coils (an example of magnetic field information of a detection target).

The magnetic-field detection results of the respective detection coils 12 are used for calculation of the position and direction information of the capsule endoscope 2 in the three-dimensional space A0 (more specifically, six variables in total of a position coordinate rc (x, y, z) of the capsule endoscope 2 and a magnetic dipole moment M (mx, my, mz) in the position coordinate rc (x, y, z)). Accordingly, it is desired that the number of arrangement of the detection coils is six or more.

The position calculator 13 functions as an arithmetic processor that calculates the position and direction of the capsule endoscope 2 in the three-dimensional space A0 of the absolute coordinate system. Specifically, the position calculator 13 temporarily sets the position coordinate rc of the capsule endoscope 2 and the magnetic dipole moment M under control of the controller 16, and calculates theoretical values of the magnetic-field detection results acquired by the respective detection coils 12 (hereinafter, "field-strength theoretical values") by using the temporarily set position coordinate rc and magnetic dipole moment M. The position calculator 13 acquires the field-strength detection values $Bd_1, \ldots, Bd_n$ acquired by the respective detection coils 12 via the controller

16. The position calculator 13 generates an evaluation function expressing an error between measurement values in the magnetic-field detection results of the respective detection coils 12 (that is, the field-strength detection values $Bd_1, \ldots, Bd_n$) and the field-strength theoretical values, and performs optimization convergence calculation based on the generated evaluation function to thereby calculate the position and direction of the capsule endoscope 2. In this case, the position calculator 13 calculates the position and direction information of the capsule endoscope 2 based on the temporary position coordinate rc and the temporary magnetic dipole moment M when an error value in the optimization convergence calculation is minimized. The position calculator 13 then transmits a result of the optimization convergence calculation when the error value is minimized, that is, the position and direction information of the capsule endoscope 2 to the controller 16. In this case, the position calculator 13 transmits to the controller 16 information of a vector p (x, y, z, mx, my, mz) including the respective components of the position coordinate rc and the magnetic dipole moment M as vector components, as the position and direction information of the capsule endoscope 2, which is a result of the optimization convergence calculation.

The input unit 14 is realized by using an input device such as a keyboard and a mouse, and inputs various pieces of information to the controller 16 in response to the input operation by the user such as a doctor or nurse. The various pieces of information input to the controller 16 by the input unit 14 includes, for example, the instruction information for instructing the controller 16 and the temporary position and direction information of the capsule endoscope 2. The temporary position and direction information is initial values of the position coordinate rc and the magnetic dipole moment M required at the time of calculating the field-strength theoretical value by the position calculator 13, and specifically, is a temporarily set value of the vector P (x, y, z, mx, my, mz).

The storage unit 15 is realized by using various storage media that rewritably store information such as a RAM, ERPROM, flash memory, or hard disk. The storage unit 15 stores various pieces of information instructed to be stored by the controller 16, and transmits information instructed to be read by the controller 16 from the stored various pieces of information. Specifically, the storage unit 15 stores convergence result information 15a of the optimization convergence calculation and area information 15b relating to a detection space of the position detecting device 10.

The convergence result information 15a is a convergence result of the optimization convergence calculation performed by the position calculator 13, and includes at least the final convergence result (the latest convergence result in time series). The convergence result is a result of the optimization convergence calculation in which the error value in the optimization convergence calculation converges to a value equal to or less than a predetermined threshold, of the optimization convergence calculations performed by the position calculator 13. The area information 15b is coordinate information for respectively specifying a determination area and an inside area to be set in the detection space of the position detecting device 10. The detection space is a space in a range in which the position detecting device 10 can detect the position and direction of a detection target (for example, the capsule endoscope 2) in the three-dimensional space A0 of the absolute coordinate system. The determination area is an area set in the detection space of the position detecting device 10 and having high reliability of the convergence result (an error between the position and direction information based on the convergence result and the actual current position and current direction of the capsule endoscope 2 is small). The inside area is set in the determination area, taking position detection accuracy of the position detecting device 10 into consideration, and reliably accommodates the position variation range of the capsule endoscope 2 calculated by the optimization convergence calculation in the determination area.

The controller 16 controls the operation of the respective components (the magnetic field detector 11, the position calculator 13, the input unit 14, and the storage unit 15) of the position detecting device 10, and also controls input and output of signals between the respective components. Specifically, the controller 16 controls information input from the magnetic field detector 11 based on the instruction information input by the input unit 14 and calculation of the position and direction information by the position calculator 13, thereby controlling detection of the position and direction information of the capsule endoscope 2, which is a detection target.

The controller 16 includes a convergence determining unit 16a that determines whether the result of the optimization convergence calculation performed by the position calculator 13 converges, an area determining unit 16b that determines a presence area of the capsule endoscope 2 in the three-dimensional space A0, and an update processor 16c that updates information such as a convergence result of the optimization convergence calculation.

The convergence determining unit 16a acquires the result of the optimization convergence calculation performed by the position calculator 13, and determines whether the acquired result of the optimization convergence calculation converges. The controller 16 stores the result of the optimization convergence calculation determined to be in a converged state by the convergence determining unit 16a (that is, a convergence result) in the storage unit 15 as a part of the convergence result information 15a. The convergence result of the optimization convergence calculation includes, for example, the information of the vector p (x, y, z, mx, my, mz) including the respective vector components of the position coordinate rc of the capsule endoscope 2 and the magnetic dipole moment M.

The area determining unit 16b determines whether the position of the capsule endoscope 2 calculated by the optimization convergence calculation by the position calculator 13 is within the determination area, and also determines whether the position of the capsule endoscope 2 is within the inside area. The controller 16 sets the determination space of the position detecting device 10, which is a space for detecting the position and direction of the capsule endoscope 2, in the three-dimensional space A0 of the absolute coordinate system, and sets the determination area in the set determination space. The controller 16 also sets the inside area in the determination area, taking the position detection accuracy of the position detecting device 10 into consideration. The area determining unit 16b determines whether the position of the capsule endoscope 2 indicated by the position and direction information (specifically, the vector p) is within the determination area or the inside area, based on the respective pieces of coordinate information and position and direction information of the determination area or the inside area. The controller 16 stores a plurality of coordinate information for defining the determination area and a plurality of pieces of coordinate information for defining the inside area in the storage unit 15 as a part of the area information 15b.

The update processor 16c updates the final convergence result of the optimization convergence calculation. Specifically, the update processor 16c designates the result of the optimization convergence calculation (the convergence result) determined to be in a converged state by the convergence determining unit 16a as the final convergence result at the present moment, and sequentially updates the acquired latest convergence result as the final convergence result, every time the convergence determining unit 16a determines that the optimization convergence calculation is in the converged state. The controller 16 stores the final convergence result defined by the update processor 16c in the storage unit 15 as a part of the convergence result information 15a. The update processor 16c expands the determination area as needed, and updates the expanded determination area as the final determination area.

Figure 2:
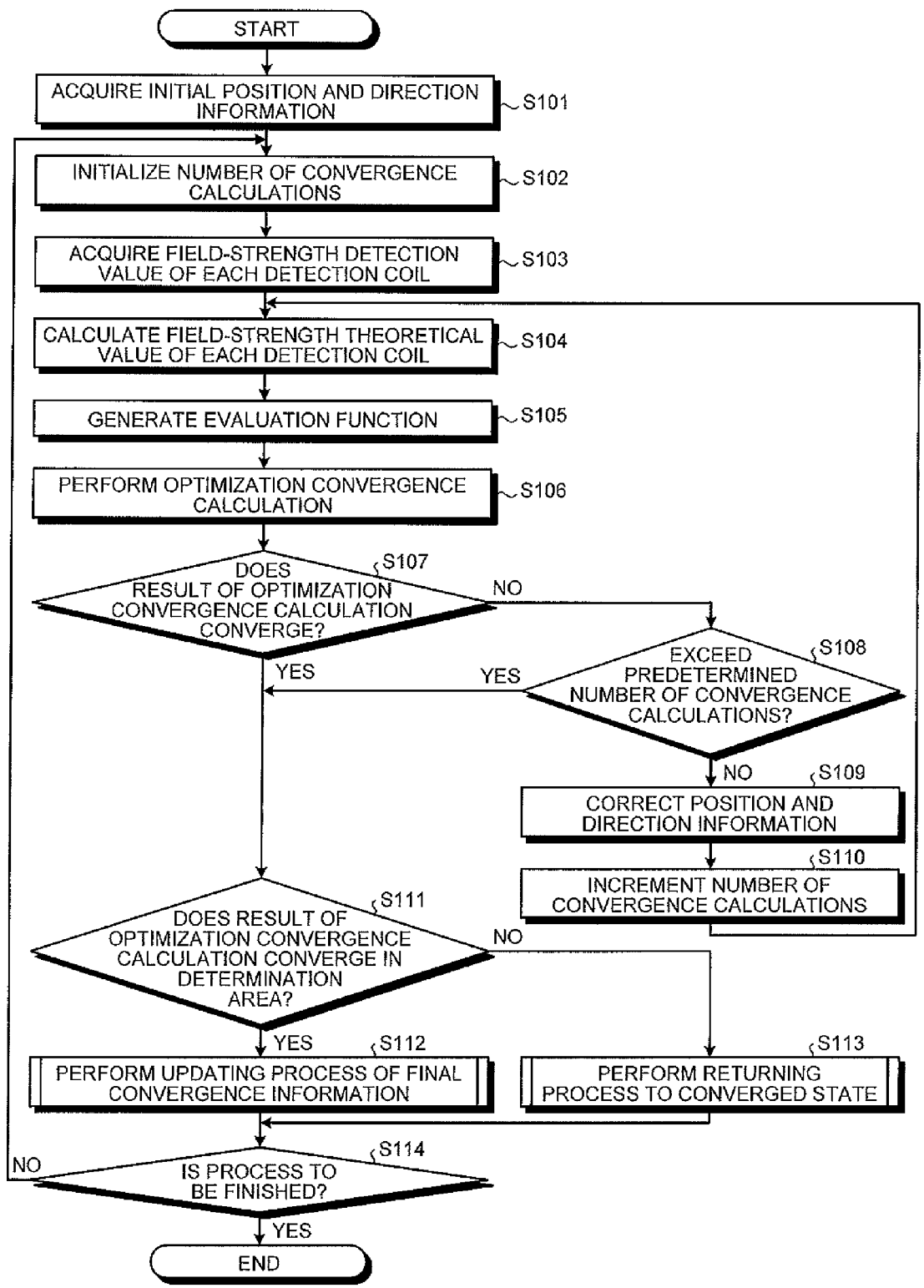
FIG. 2 is a flowchart exemplifying a process procedure performed by a controller in a position detection device according to the first embodiment.

An operation of the position detecting device 10 according to the first embodiment of the present invention is explained next. FIG. 2 is a flowchart exemplifying a process procedure performed by the controller 16 in the position detection device 10 according to the first embodiment. When the position detecting device 10 detects the position and direction information of the capsule endoscope 2 in a subject, the controller 16 controls the information input from the magnetic field detector 11 and various types of arithmetic processing performed by the position calculator 13, to control detection of the position and direction information of the capsule endoscope 2.

Specifically, as shown in FIG. 2, the controller 16 acquires initial position and direction information input by the input unit 14 (Step S101), and initializes the number of convergence calculations of the optimization convergence calculation performed by the position calculator 13 to zero (Step S102). The initial position and direction information is, for example, initial information temporarily set by referring to an initial position of the capsule endoscope 2 in the three-dimensional space A0 (specifically, in a subject), and includes information of a temporary vector p. The controller 16 transmits the initial position and direction information to the position calculator 13.

The controller 16 then acquires, from the magnetic field detector 11, the field-strength detection values $Bd_1, \ldots, Bd_n$ acquired by the respective detection coils 12 (Step S103). At Step S103, the controller 16 acquires, a predetermined average number of times, the field-strength detection value for each of n detection coils 12. The controller 16 performs, for each detection coil, a movement averaging process with respect to the field-strength detection values $Bd_1, \ldots, Bd_n$ each of which has been acquired the average number of times. The controller 16 can reduce, by the movement averaging process, position variation factors concerning the capsule endoscope 2 that are included in the field-strength detection values $Bd_1, \ldots, Bd_n$. The controller 16 transmits the movement-averaged field-strength detection values $Bd_1, \ldots, Bd_n$ of the respective detection coils 12 to the position calculator 13.

When performing the movement averaging process, the controller 16 can select the required number of field-strength detection values (for example, six or more) of the detection coils to be used for the optimization convergence calculation by the position calculator 13 from the respective field-strength detection values $Bd_1, \ldots, Bd_n$ of the n detection coils 12, to perform the movement averaging process respectively for the selected field-strength detection values.

Subsequently, the controller 16 causes the position calculator 13 to calculate the field-strength theoretical value of each of the detection coils 12 corresponding to the field-strength detection values used for the optimization convergence calculation (Step S104). At Step S104, the controller 16 transmits the temporary vector p (x, y, z, mx, my, mz) representing the temporary position and direction information of the capsule endoscope 2 and the position coordinate $rs_i$ (i is an integer of 1 to n) of each of the detection coils 12 to the position calculator 13. When the number of convergence calculations performed by the position calculator 13 is the first, the temporary vector p indicates the initial position and direction information input at Step S101, and when the number of convergence calculations by the position calculator 13 is the second or thereafter, the temporary vector p indicates the final convergence result by the previous optimization convergence calculation. The position calculator 13 calculates the field-strength detection theoretical value of each of the detection coils 12 based on the temporary vector p and the position coordinate $rs_i$ of the detection coil 12 under control of the controller 16.

Specifically, the position calculator 13 temporarily sets the position coordinate rc (x, y, z) of the capsule endoscope 2 in the three-dimensional space A0 and the magnetic dipole moment M (mx, my, mz) in the position coordinate, based on the temporary vector p acquired from the controller 16. The position calculator 13 then calculates a distance vector $r_i$ (xi-1, yi-y, zi-z) between the position coordinate rc (x, y, z) and the position coordinate $rs_i$ (xi, yi, zi) of ith detection coil 12. The ith is a number for specifying each of the detection coils 12 and i is an integer of 1 to n. The position calculator 13 calculates the field-strength theoretical value $B_i$ by using the magnetic dipole moment M, the position coordinate rc, and the distance vector $r_i$. The field-strength theoretical value $B_i$ is a theoretical value of the magnetic detection result when the ith detection coil 12 detects the magnetic field by the magnetic dipole moment M (specifically, the magnetic field generated by the magnetic field generator 2b), and is calculated based on the following equation (1). The position calculator 13 repeatedly performs arithmetic processing based on the equation (1) to calculate magnetic-field theoretical values $B_1, \ldots, B_n$ of 1st to nth detection coils 12.

$$B_i = \frac{1}{4\pi}\left\{\frac{3(M \cdot r_i)}{r_i^5}r_i - \frac{M}{r_i^3}\right\} \quad (1)$$

The controller 16 then causes the position calculator 13 to generate the evaluation function expressing an error between the magnetic-field detection value and the field-strength theoretical value of each of the detection coils 12 (Step S105), and causes the position calculator 13 to perform the optimization convergence calculation based on the generated evaluation function (Step S106). In this case, the position calculator 13 generates the evaluation function expressing an error (for example, a square error) between the magnetic-field detection values $Bd_1, \ldots, Bd_n$ and the field-strength theoretical values $B_1, \ldots, B_n$ of the respective detection coils 12 under control of the controller 16. The evaluation function generated by the position calculator 13 is expressed by the following equation (2).

$$\sum_{i=1}^{n}(Bd_i - B_i(p))^2 = 0 \quad (2)$$

The position calculator 13 performs the optimization convergence calculation based on the evaluation function expressed by the equation (2) to calculate the position and direction of the capsule endoscope 2 under control of the controller 16. In this case, the position calculator 13 calculates the vector p (x, y, z, mx, my, mz) including, as the vector component, the temporary position coordinate rc and the temporary magnetic dipole moment M when an error value in the optimization convergence calculation is minimized, as the position and direction information of the capsule endoscope 2.

The controller 16 then determines whether the result of the optimization convergence calculation performed by the position calculator 13 converges (Step S107). At Step S107, the convergence determining unit 16a acquires the error value in the optimization convergence calculation from the position calculator 13, and compares the error value with a predetermined threshold. When the error value is larger than the threshold, the convergence determining unit 16a determines that the result of the optimization convergence calculation has not converged (that is, in a diverged state).

When the result of the optimization convergence calculation performed by the position calculator has not converged (NO at Step S107), the controller 16 determines whether the number of executions of the optimization convergence calculation exceeds the predetermined number of convergence calculations (Step S108). When the number of executions of the optimization convergence calculation is equal to or less than the predetermined number of convergence calculations, that is, when the position calculator 13 has not performed the optimization convergence calculation for the specified number of convergence calculations (NO at Step S108), the controller 16 corrects the temporarily set position and direction information (Step S109). At Step S109, the controller 16 corrects respective variables (that is, vector components) of the temporary vector p representing the temporary position and direction information, and designates the corrected temporary vector p as a starting point of calculation for the next optimization convergence calculation. Thereafter, the controller 16 increments the number of convergence calculations performed by the position calculator 13 (Step S110), and returns to Step S104 to repeat a process procedure at Step S104 and subsequent steps.

At Step S107, when the error value in the optimization convergence calculation performed by the position calculator 13 is equal to or less than a predetermined threshold, the convergence determining unit 16a determines that the result of the optimization convergence calculation converges (that is, the error value in the optimization convergence calculation is in a converged state). When the result of the optimization convergence calculation converges (YES at Step S107), the controller 16 determines whether the result of the optimization convergence calculation converges in the determination area (Step S111).

At Step S111, the area determining unit 16b determines whether the position coordinate of the capsule endoscope 2 indicated by the vector p based on the convergence result of the optimization convergence calculation is within the determination area. When the position coordinate of the capsule endoscope 2 is within the determination area, the area determining unit 16b determines that the result of the optimization convergence calculation converges in the determination area. When the position coordinate is outside the determination area, the area determining unit 16b determines that the result of the optimization convergence calculation pseudo-converges outside the determination area (that is, the result of the optimization convergence calculation is in a diverged state). When the result of the optimization convergence calculation converges in the determination area (YES at Step S111), the controller 16 updates the final convergence information of the optimization convergence calculation performed by the position calculator 13 (Step S112). The final convergence information of the optimization convergence calculation includes the vector p based on the convergence result (position and direction information of the capsule endoscope 2), the determination area at the time of acquiring the convergence result, and the like. When the result of the optimization convergence calculation has pseudo-converged outside the determination area, the controller 16 performs a returning process of returning the diverged state of the optimization convergence calculation to a converged state (Step S113).

The controller 16 determines whether the process is to be finished after performing Step S112 or S113 (Step S114). When the process is not finished (NO at Step S114), the controller 16 returns to Step S102 and repeats the process procedure at Step S102 and subsequent steps. For example, when the input unit 14 inputs instruction information instructing to finish the process, the controller 16 determines to finish the process (YES at Step S114), and the process is finished.

At Step S108, when the number of executions of the optimization convergence calculation exceeds the predetermined number of convergence calculations (YES at Step S108), the controller 16 proceeds to Step S111 to repeat the process procedure at Step S111 and subsequent steps. In this case, the convergence determining unit 16a determines that the result of the optimization convergence result has not converged (that is, the error value in the optimization convergence calculation is in a diverged state) based on a fact that the number of executions of the optimization convergence calculation exceeds the predetermined number of convergence calculations. Accordingly, the controller 16 determines that the result of the optimization convergence calculations has not converged in the determination area at Step S111 (NO at Step S111), and proceeds to Step S113 to repeat the process procedure at Step S113 and subsequent steps.

Figure 3:
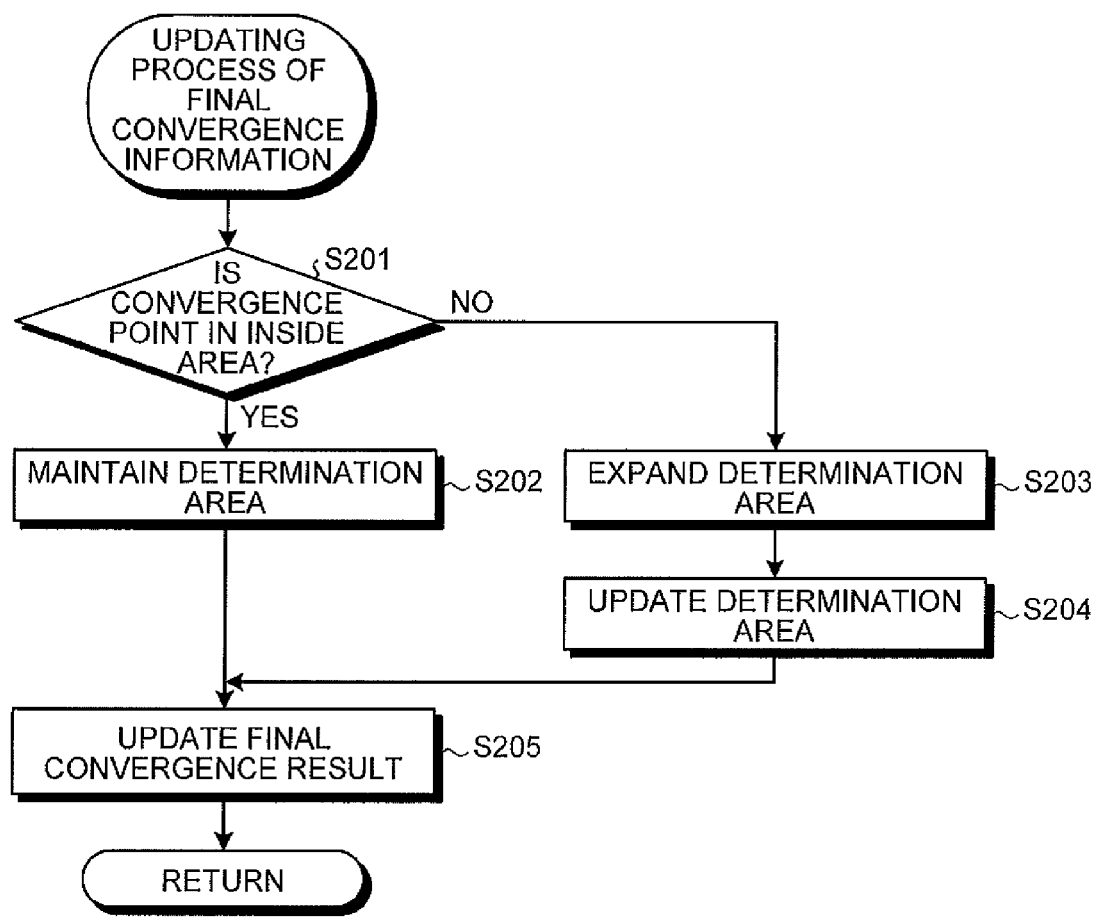
FIG. 3 is a flowchart exemplifying a process procedure until the controller in the position detecting device according to the first embodiment completes an updating process of final convergence information.

An updating process of the final convergence information (Step S112) is explained next. FIG. 3 is a flowchart exemplifying a process procedure until the controller 16 in the position detecting device 10 according to the first embodiment completes the updating process of the final convergence information. As shown in FIG. 3, when the result of the optimization convergence calculation performed by the position calculator 13 converges in the determination area, the controller 16 further determines whether the position of the capsule endoscope 2 indicated by the vector p based on the convergence result of the optimization convergence calculation (hereinafter, "convergence point") is in the inside area (Step S201). At Step S201, the area determining unit 16b reads a plurality of pieces of coordinate information (for example, eight corners of a cube) specifying the inside area from the area information 15b in the storage unit 15, and determines whether the convergence point is in the inside area based on the read coordinate information of the inside area and the vector component of the vector p.

When the convergence point is in the inside area (YES at Step S201), the controller 16 maintains the determination area set outside the inside area (Step S202). That is, when the position coordinate of the capsule endoscope 2 calculated by the optimization convergence calculation is in the inside area, the controller 16 maintains the coordinate information of the determination area at the present moment, and does not change the determination area.

When the convergence point based on the convergence result of the optimization convergence calculation is outside the inside area (NO at Step S201), the controller 16 expands the determination area outside the inside area (Step S203), and updates the determination area (Step S204). At Steps S203 and S204, the update processor 16c expands the determination area corresponding to the position detection accuracy (specifically, the position variation range of the convergence point of the capsule endoscope 2) of the position detecting device 10, and sets the determination area in which the position variation range of the convergence point is included in the area. The update processor 16c updates the expanded determination area as the final determination area. The coordinate information for defining the final determination area after the update is stored in the storage unit 15 as a part of the area information 15b.

The controller 16 having performed the process procedure at Step S202 or S204 updates the convergence result of the optimization convergence calculation for calculating the convergence point (specifically, the vector p representing the convergence point) as the final convergence result (Step S205), and returns to Step S112. The final convergence result after the update is stored in the storage unit 15 as a part of the convergence result information 15a. The vector p corresponding to the final convergence result is used as the starting point of calculation for the next optimization convergence calculation.

Figure 4:
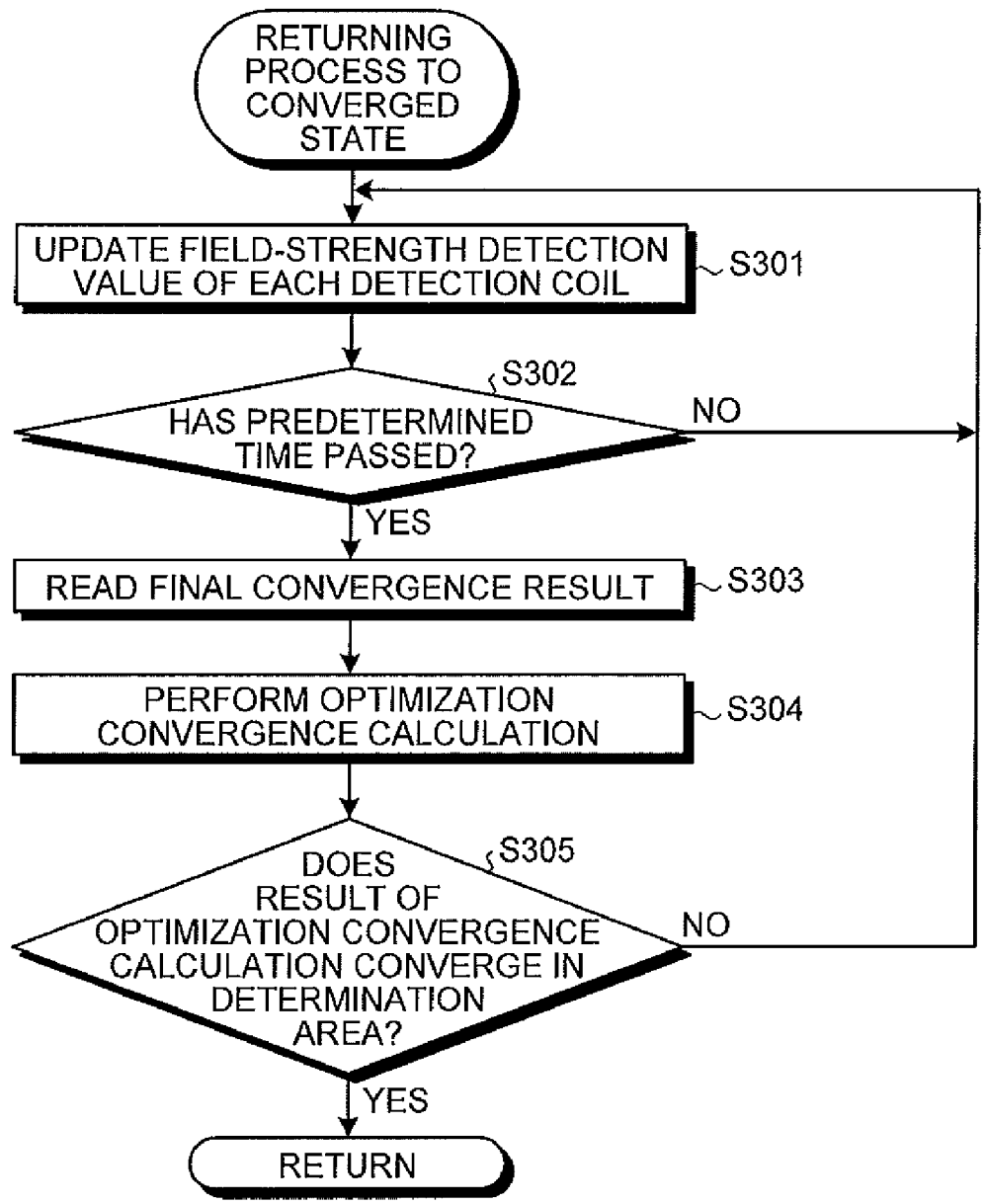
FIG. 4 is a flowchart exemplifying a process procedure until the controller in the position detecting device according to the first embodiment completes a returning process of a converged state of optimization convergence calculation.

The returning process of a converged state of the optimization convergence calculation (Step S113) is explained next. FIG. 4 is a flowchart exemplifying a process procedure until the controller 16 in the position detecting device 10 according to the first embodiment completes the returning process to a converged state of the optimization convergence calculation.

As shown in FIG. 4, when the result of the optimization convergence calculation performed by the position calculator 13 does not converge in the determination area, the controller 16 newly acquires the field-strength detection values of the respective detection coils used for the optimization convergence calculation, to update the respective field-strength detection values to be used for the optimization convergence calculation (Step S301). When a predetermined time has not passed since acquisition of the field-strength detection values of the respective detection coils 12 at Step S103 (NO at Step S302), the controller 16 repeats the process procedure at Step S301. The controller 16 repeats the process procedure at Steps S301 and S302 until the predetermined time passes, to suspend the arithmetic processing of the position calculator 13 such as optimization convergence calculation for a predetermined period of time.

When the result of the optimization convergence calculation diverges, it is possible that the field-strength detection values of the respective detection coils 12 used for the optimization convergence calculation have been adversely affected by a disturbance such as noise. The controller 16 suspends the arithmetic processing of the position calculator 13 for a predetermined time and invalidates, from older ones, the field-strength detection values of the respective detection coils 12. The predetermined time may be a time corresponding to a multiplication value of the average number of times, which the field-strength detection value is detected for the movement averaging process, and a sampling time required for acquiring one field-strength detection value from the respective detection coils 12. With this, the field-strength detection value that caused the divergence of the result of the optimization convergence calculation can be eliminated.

When such a predetermined time passes (YES at Step S302), the controller 16 reads the final convergence result of the position calculator 13 from the convergence result information 15a in the storage unit 15 (Step S303), and transmits the read final convergence result and the field-strength detection values of the respective detection coils 12 updated at Step S301 (specifically, respective field-strength detection values subjected to the movement averaging process for each detection coil) to the position calculator 13. The controller 16 causes the position calculator 13 to perform the optimization convergence calculation using the field-strength detection values of the respective detection coils 12 and the final convergence result (the vector p representing the final convergence point) (Step S304). The final convergence result used for the optimization convergence calculation at Step S304 indicates a convergence point (the vector p) included in the determination area (for example, the determination area before being expanded by the update processor 16c).

At Step S304, the position calculator 13 temporarily sets the position coordinate re (x, y, z) of the capsule endoscope 2 and the magnetic dipole moment M (mx, my, mz) based on the vector p acquired as the final convergence result, and recalculates the field-strength theoretical values $B_1, \ldots, B_n$ based on the equation (1) by using the temporarily set position coordinate rc and magnetic dipole moment M (mx, my, mz). The position calculator 13 then generates the evaluation function (see the equation (2)) expressing an error between the recalculated field-strength theoretical values $B_1, \ldots, B_n$ and the field-strength detection values $Bd_1, \ldots, Bd_n$ reacquired at Steps S301 and S302, and performs once the optimization convergence calculation based on the generated evaluation function. The position calculator 13 transmits a result of the optimization convergence calculation performed once to the controller 16.

The controller 16 acquires the result of the optimization convergence calculation performed by the position calculator 13 at Step S304, to determine whether the acquired result of the optimization convergence calculation converges in the determination area (Step S305). At Step S305, the convergence determining unit 16a determines whether the error value in the one optimization convergence calculation converges to a value equal to or less than a predetermined threshold, and the area determining unit 16b determines whether the position of the capsule endoscope 2 indicated by the vector p calculated by the one optimization convergence calculation is in the determination area. When the result of the one optimization convergence calculation converges in the determination area (YES at Step S305), it means that the diverged state of the optimization convergence calculation performed by the position calculator 13 returns to a converged state, and the controller 16 returns to Step S113.

In contrast, when the result of the one optimization convergence calculation has not converged in the determination area (NO at Step S305), the controller 16 returns to Step S301 to repeat the process procedure at Step S301 and subsequent steps.

When the error value of the one optimization convergence calculation converges to a value equal to or less than the predetermined threshold, and the position of the capsule endoscope 2 indicated by the vector p calculated by the one optimization convergence calculation is in the determination area, the result of the one optimization convergence calculation is determined as having converged in the determination area. When the error value of the one optimization convergence calculation is larger than the predetermined threshold or the position of the capsule endoscope 2 indicated by the vector p calculated by the one optimization convergence calculation is outside the determination area, the result of the one optimization convergence calculation is determined as having not converged in the determination area.

Figure 5:
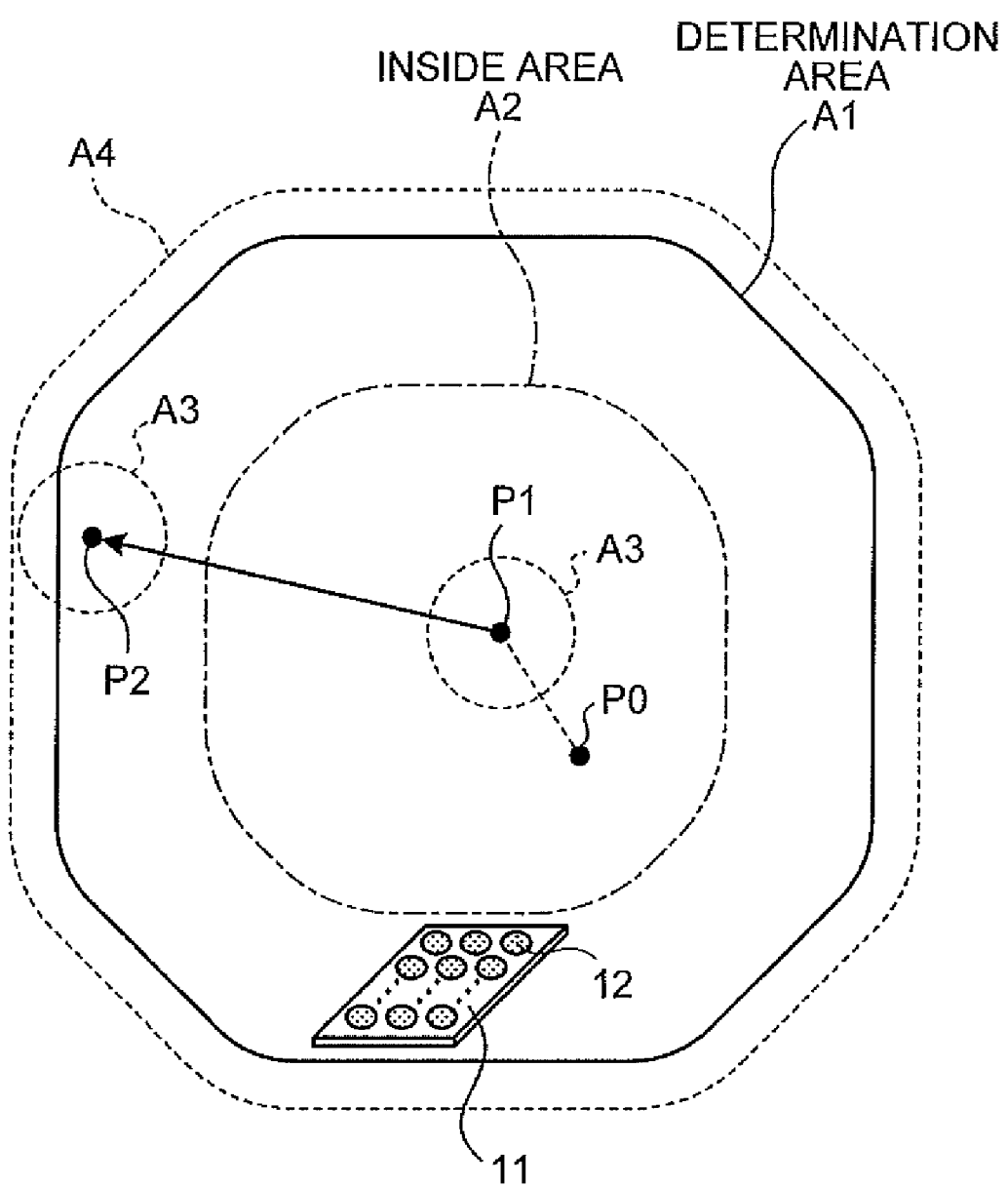
FIG. 5 is a schematic diagram specifically explaining the updating process of the final convergence information of the optimization convergence calculation and the returning process of the converged state.

The updating process (Step S112) of the final convergence information including the final convergence result of the optimization convergence calculation and the determination area and the returning process to a converged state (Step S113) are explained next in detail. FIG. 5 is a schematic diagram specifically explaining the updating process of the final convergence information of the optimization convergence calculation and the returning process to the converged state. In FIG.

5, positions P0, P1, and P2 are positions of the capsule endoscope 2 sequentially calculated by the optimization convergence calculation performed by the position calculator 13, where the position P2 is a position coordinate calculated subsequent to the position P1, and the position P0 is a convergence point calculated prior to the position P1.

As shown in FIG. 5, the controller 16 sets a determination area A1 in the three-dimensional space in which the magnetic field detector 11 can normally detect the magnetic field by a plurality of the detection coils 12, and sets an inside area A2 in the determination area A1 (for example, an area including a central part of the determination area A1), taking a position variation range A3 of the capsule endoscope 2 into consideration. In this case, the inside area A2 is an area capable of reliably accommodating the position variation range A3 of the capsule endoscope 2 in the determination area A1. That is, the position of the capsule endoscope 2 in the inside area A2 (for example, the position P1) is reliably accommodated in the determination area A1 together with the position variation range A3. This means that there is little possibility that the position of the capsule endoscope 2 in the inside area A2 cannot be detected suddenly.

The controller 16 determines whether the result of the optimization convergence calculation at the time of calculating the position P1 of the capsule endoscope 2 converges in the determination area A1. In this case, the convergence determining unit 16a determines whether the error value in the optimization convergence calculation corresponding to the position P1 converges to a value equal to or less than the predetermined threshold, and the area determining unit 16b determines whether the position P1 is in the determination area A1. When the convergence determining unit 16a and the area determining unit 16b determine that the result of the optimization convergence calculation converges and the position P1 is in the determination area A1, the controller 16 determines that the optimization convergence calculation corresponding to the position P1 converges in the determination area A1, and acquires the position P1 as the convergence point of the capsule endoscope 2.

When the position P1 is the convergence point in the determination area A1, the area determining unit 16b further determines whether the position P1 is the convergence point in the inside area A2. When the position P1 is the position coordinate in the inside area A2 as shown in FIG. 5, the area determining unit 16b determines that the position P1 is the convergence point in the inside area A2. In this case, the controller 16 maintains the determination area A1, and the update processor 16c updates the vector p (x, y, z, mx, my, mz) representing the position P1 as the final convergence result.

When causing the position calculator 13 to calculate the position P2 subsequent to the position P1, the controller 16 designates the final convergence result (the vector p) corresponding to the position P1 as the starting point of calculation for the next optimization convergence calculation. The position calculator 13 temporarily sets the position coordinate rc of the capsule endoscope 2 and the magnetic dipole moment M by using the final convergence result corresponding to the position P1, to calculate the field-strength theoretical values $B_1, \ldots, B_n$, based on the equation (1). The position calculator 13 generates the evaluation function (see the equation (2)) by using the calculated field-strength theoretical values $B_1, \ldots, B_n$ and the field-strength detection values $Bd_1, \ldots, Bd_n$, of the respective detection coils 12, and performs the optimization convergence calculation based on the generated evaluation function to calculate the vector p representing the position P2 of the capsule endoscope 2.

The controller 16 determines whether the result of the optimization convergence calculation converges in the determination area A1 for the position P2 of the capsule endoscope 2, as in the case of the position P1. Specifically, when the convergence determining unit 16a determines that the result of the current optimization convergence calculation converges and the area determining unit 16b determines that the position P2 is in the determination area A1, the controller 16 determines that the optimization convergence calculation corresponding to the position P2 converges in the determination area A1, and acquires the position P2 as the convergence point of the capsule endoscope 2.

When the position P2 is the convergence point in the determination area A1, the area determining unit 16b further determines whether the position P2 is the convergence point in the inside area A2. The inside area A2 is smaller than the determination area A1 by at least the space corresponding to the position variation range of the capsule endoscope 2, and is set inside of the determination area A1 by the controller 16. When the position P2 is the position coordinate outside the inside area A2 as shown in FIG. 5, the area determining unit 16b determines that the position P2 is the convergence point outside the inside area A2. In this case, the update processor 16c expands the determination area A1 to a determination area A4 corresponding to the position variation range A3 of the position P2 (that is, sets the determination area A4 acquired by expanding the determination area A1 by the space corresponding to the position variation range A3), and updates the expanded determination area A4 as the final determination area. In this case, the position variation range A3 of the position P2 is accommodated in the expanded determination area A4. The update processor 16c updates the vector p (x, y, z, mx, my, mz) representing the position P2 as the final convergence result.

When the result of the optimization convergence calculation at the time of calculating the position P1 of the capsule endoscope 2 does not converge in the determination area A1, the controller 16 invalidates, from older ones, the field-strength detection values of the respective detection coils 12 and suspends the arithmetic processing of the position calculator 13 until a predetermined time (a time corresponding to a multiplication value of the average number of times for the movement averaging process and the sampling time required for acquiring the field-strength detection value) passes. With this, the field-strength detection values corresponding to the number of times for movement averaging are updated for the respective detection coils 12. When the position P1 is not the convergence point, the controller 16 causes the position calculator 13 to perform the optimization convergence calculation, designating the final convergence result corresponding to the position P0, which is the latest convergence point of the convergence points of the position P1 calculated previously as the starting point of calculation for the next optimization convergence calculation. The position P0 corresponding to the final convergence result is the convergence point in the determination area A1 before expansion.

The position calculator 13 performs the optimization convergence calculation designating the final convergence result (the vector p) corresponding to the position P0 as the starting point of calculation under control of the controller 16 to calculate the vector p. When the optimization convergence calculation converges in the determination area, the controller 16 can return the result of the optimization convergence calculation, which has been a diverged state previously, to a converged state in a short period of time. The controller 16 causes the position calculator 13 to perform the optimization convergence calculation designating the convergence result of the optimization convergence calculation as the starting point of calculation for the next optimization convergence calculation.

In the first embodiment, as described above, the magnetic field from the magnetic field generator incorporated in a detection target such as a capsule endoscope is detected by the plurality of detection coils, and the optimization convergence calculation based on the evaluation function expressing an error between the measurement value (the detection value) in the respective magnetic-field detection results acquired by the detection coils and the theoretical value is performed by the arithmetic processor. It is determined whether the error value in the optimization convergence calculation performed by the arithmetic processor converges. When the error value in the optimization convergence calculation converges, the position and direction information of the detection target based on the convergence result of the optimization convergence calculation is calculated, and the convergence result is set as the starting point of calculation for the next optimization convergence calculation. When the error value in the optimization convergence calculation does not converge (diverges), arithmetic processing of the arithmetic processor such as optimization convergence calculation is suspended until a predetermined time passes, to acquire the measurement value in the respective magnetic-field detection results acquired by the detection coils again, and the optimization convergence calculation is restarted by the arithmetic processor, using the final convergence result acquired by the previous optimization convergence calculation as the starting point of calculation. Accordingly, the measurement value in the magnetic-field detection result adversely affected by a disturbance such as noise at the time of detecting the magnetic field generated from the magnetic field generator by the detection coils can be eliminated, and it is possible to prevent a case that the result of the optimization convergence calculation at the time of divergence of the error value (an uncertain arithmetic result) is used for the starting point of calculation for the next optimization convergence calculation. Accordingly, even if the error value in the optimization convergence calculation diverges, the convergence result of the optimization convergence calculation can be reliably used as the starting point of calculation for the next optimization convergence calculation. As a result, a position detecting device that can return a diverged state of the optimization convergence calculation to a converged state in a short period of time, when the error value in the optimization convergence calculation for calculating the position information and direction information of the detection target diverges, can be realized.

The determination area is set in the detection space of the position and direction of the detection target, and it is determined whether the position coordinate of the detection target based on the convergence result of the optimization convergence calculation is in the determination area. When the coordinate is in the determination area, the convergence result of the optimization convergence calculation, which has calculated the position coordinate in the determination area, is designated as the starting point of calculation for the next optimization convergence calculation. When the position coordinate is outside the determination area, it is determined that the optimization convergence calculation, which has calculated a position coordinate outside the determination area, is in a diverged state, and the arithmetic processing of the arithmetic processor such as optimization convergence calculation is suspended until a predetermined time passes, to acquire the measurement value in the respective magnetic-field detection results again, and the optimization convergence calculation is restarted by the arithmetic processor, using the final convergence result acquired by the previous optimization convergence calculation as the starting point of calculation. Accordingly, it is possible to prevent a case that an uncertain result of the optimization convergence calculation such as a result of the optimization convergence calculation when the error value pseudo-converges is used as the starting point of calculation for the next optimization convergence calculation, thereby enabling to calculate the position and direction of the detection target highly accurately, and the converged state of the optimization convergence calculation can be maintained easily.

Further, the inside area for accommodating the position variation range of the detection target is set in the determination area, and it is determined whether the position coordinate of the detection target based on the convergence result of the optimization convergence calculation is in the convergence determination stability. When the position coordinate is in the inside area, the current determination area is maintained. When the position coordinate is outside the determination area, the determination area is expanded corresponding to the position variation range of the detection target, and the expanded determination area is updated to the determination area at the time of performing the next optimization convergence calculation. Accordingly, the determination area can be easily expanded, matched with the detection accuracy of the position detecting device, thereby enabling to control a state such that the optimization convergence calculation in which the error value has actually converged is erroneously determined to be in a diverged state and prevent a case that the optimization convergence calculation frequently diverges. As a result, the processing time of arithmetic processing such as optimization convergence calculation for calculating the position and direction information of the detection target can be shortened.

Second Embodiment

A second embodiment of the present invention is explained next. In the first embodiment, the magnetic field formed by the magnetic field generator $2b$ incorporated in the capsule endoscope 2 as a detection target, is detected by the detection coils 12. However, in the second embodiment, the magnetic field is applied to an LC marker incorporated in the capsule endoscope as the detection target, and a generated induced magnetic field of the LC marker is detected by the detection coils 12.

Figure 6:
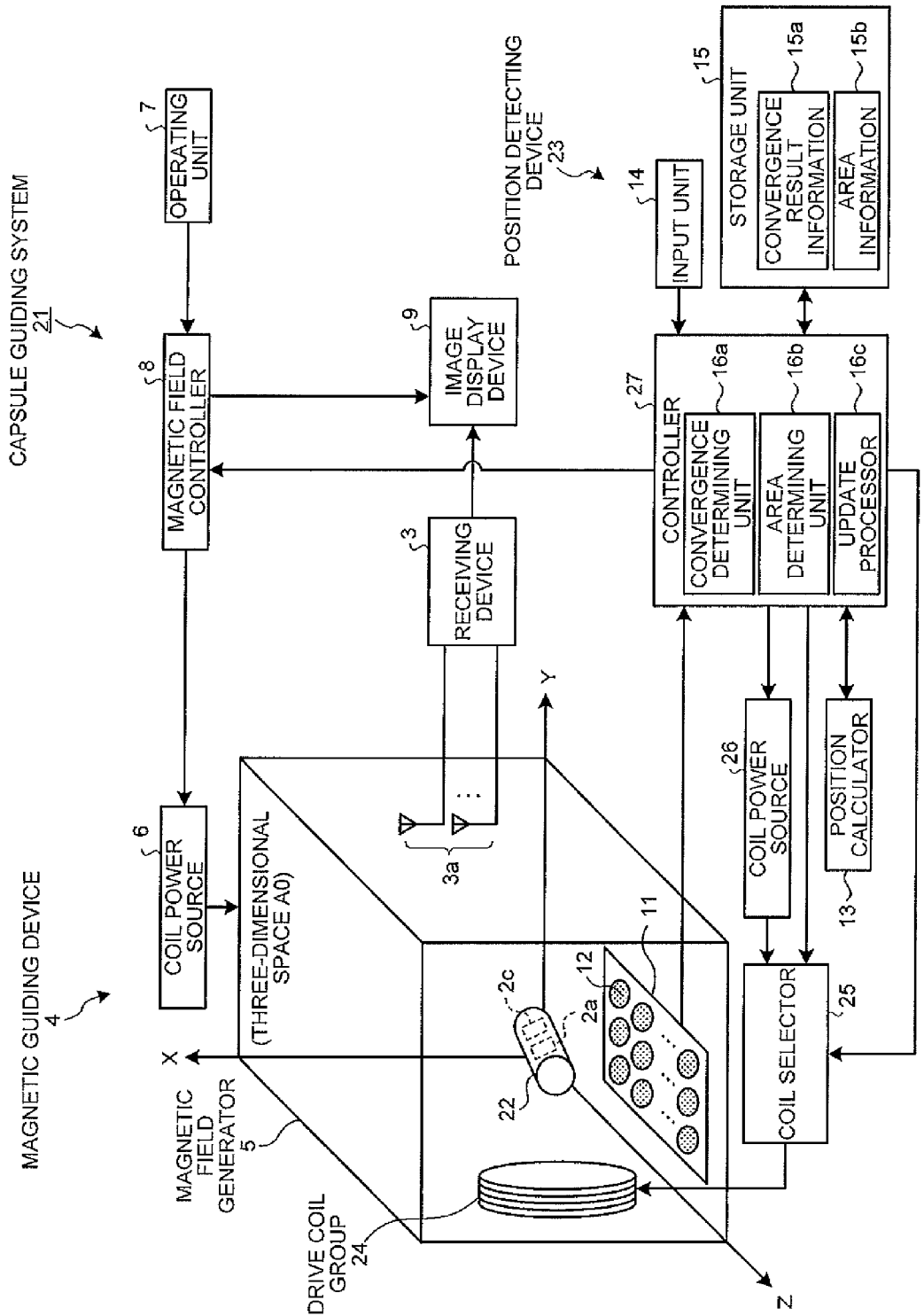
FIG. 6 is a block diagram schematically depicting a configuration example of a capsule guiding system according to a second embodiment of the present invention.

FIG. 6 is a block diagram schematically depicting a configuration example of a capsule guiding system according to the second embodiment of the present invention. As shown in FIG. 6, a capsule guiding system 21 according to the second embodiment includes a capsule endoscope 22 instead of the capsule endoscope 2 of the capsule guiding system 1 according to the first embodiment, and includes a position detecting device 23 instead of the position detecting device 10. The capsule endoscope 22 includes an LC marker $2c$ instead of the magnetic field generator $2b$. The position detecting device 23 includes a drive coil group 24 that applies the magnetic field to the LC marker $2c$, a coil selector 25 that selects a drive coil that generates the magnetic field from the drive coil group 24, and a coil power source 26 that supplies electric current for generating the magnetic field to the drive coil group 24, and includes a controller 27 instead of the controller 16. Other configurations of the second embodiment are the same as those of the first embodiment, and like components are denoted by like reference numerals.

The capsule endoscope 22 is the same as the capsule endoscope 2 in the first embodiment except for including the LC marker 2c instead of the magnetic field generator 2b. The LC marker 2c emits an induced magnetic field due to an action of the magnetic field applied by the drive coil group 24 in the position detecting device 23. Accordingly, there is a more suitable drive coil depending on the direction of the LC marker 2c. The induced magnetic field generated by the LC marker 2c is detected by the detection coils 12 in the magnetic field detector 11. In this case, the field-strength detection values $Bd_1, \ldots, Bd_n$ of the induced magnetic field detected by the detection coils 12 in the magnetic field detector 11 are an example of the magnetic field information of the detection target and are acquired by the controller 27.

The drive coil group 24 is realized by a plurality of magnetic-field generation coils (drive coils) that generates the magnetic field for detecting the position and direction information of the capsule endoscope 22 in a subject. The drive coil group 24 applies the magnetic field of strength and direction appropriate to the current position of the LC marker 2c in the three-dimensional space A0 and a coil axis direction to the LC marker 2c, and causes the LC marker 2c to emit the induced magnetic field due to the action of the applied magnetic field.

The coil selector 25 functions as a switching unit of the drive coil, and selects one or more drive coils that generate the magnetic field from the drive coil group 24 under control of the controller 27. The one or more drive coils selected by the coil selector 25 generate the magnetic field of the appropriate strength and direction as the magnetic field that penetrates the LC marker 2c in the coil axis direction at the current position of the LC marker 2c in the three-dimensional space A0.

The coil power source 26 includes a plurality of power sources corresponding to the number of drive coils included in the drive coil group 24, and supplies the alternating current to the one or more drive coils selected in the drive coil group 24 by the coil selector 25 under control of the controller 27. In this case, the alternating current generated by the coil power source 26 is applied to the selected one or more drive coils of the drive coil group 24 via the coil selector 25, and generates the magnetic field in the one or more drive coils.

The controller 27 controls the drive coil group 24, the coil selector 25, and the coil power source 26. Specifically, the controller 27 causes the coil selector 25 to select one or more drive coils of the drive coil group 24. The controller 27 controls the energization amount of the coil power source 26 with respect to the one or more drive coils selected by the coil selector 25, and controls the magnetic-field generation operation of the drive coil group 24 through control of the energization amount. The controller 27 acquires field-strength detection values $Bd_1, \ldots, Bd_n$ of the induced magnetic field of the LC marker 2c detected by the detection coils 12 from the magnetic field detector 11. The controller 27 calculates the respective field-strength theoretical values $B_1, \ldots, B_n$ of the induced magnetic field based on the equation (1) mentioned above, and causes the position calculator 13 to perform the optimization convergence calculation based on the evaluation function (see the equation (2)) expressing an error value between the respective field-strength detection values $Bd_1, \ldots, Bd_n$ and the respective field-strength theoretical values $B_1, \ldots, B_n$ of the induced magnetic field. The controller 27 controls the switching operation of the drive coil group 24 in addition to the control for suspending the arithmetic processing of the position calculator 13 until a predetermined time passes, in the returning process of returning the diverged state of the optimization convergence calculation to the converged state. Other functions of the controller 27 are the same as those of the controller 16 in the position detecting device 10 according to the first embodiment.

An operation of the position detecting device 23 according to the second embodiment of the present invention is explained next. When the position detecting device 23 detects the position and direction information of the capsule endoscope 22 in the subject, the controller 27 repeatedly performs the process procedure substantially the same as the process procedure (Steps S101 to S114, see FIG. 2) of the controller 16 in the position detecting device 10 according to the first embodiment. In this case, the controller 27 performs control for switching the drive coil group 24 instead of the returning process to a converged state at Step S113, following the control for suspending the arithmetic processing of the position calculator 13, to perform the returning process of returning the diverged state of the optimization convergence calculation to a converged state.

Figure 7:
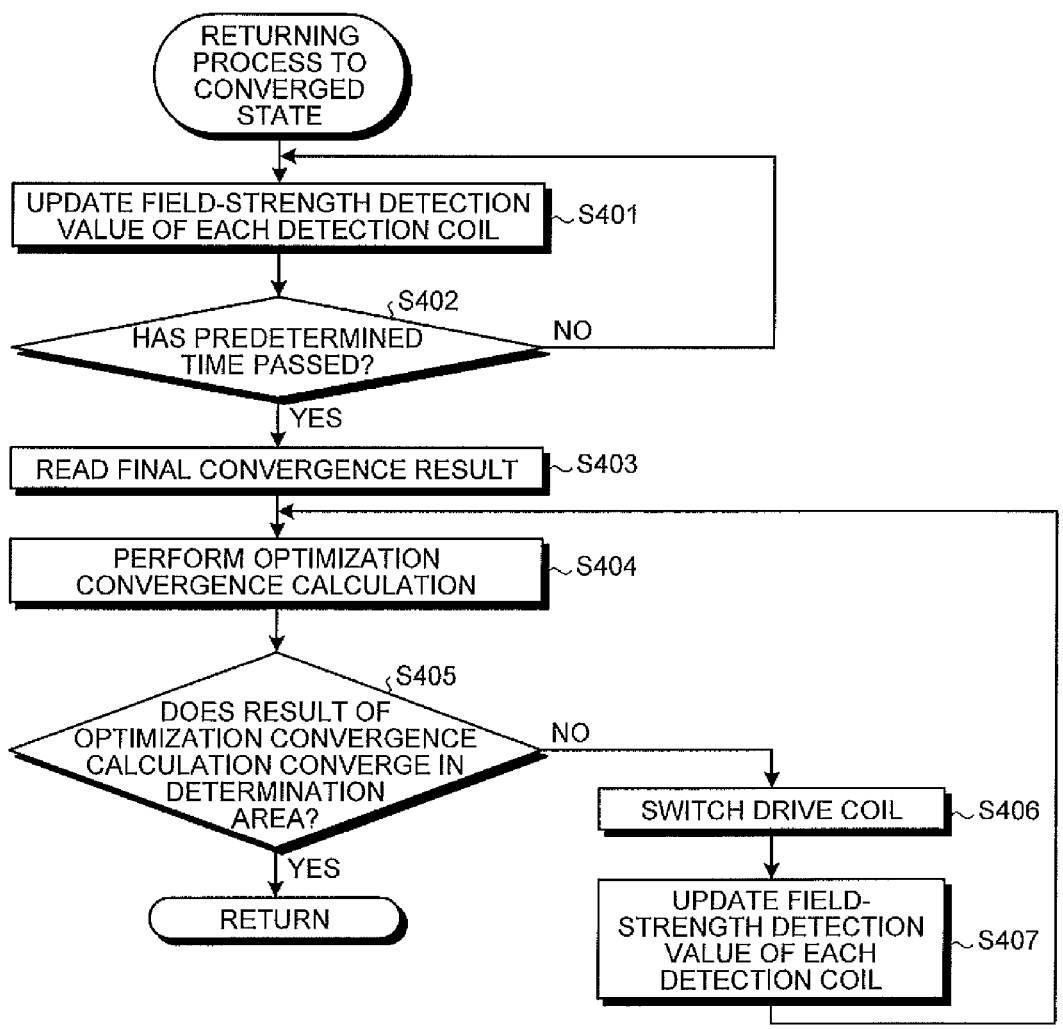
FIG. 7 is a flowchart of a process procedure until a controller in a position detecting device according to the second embodiment completes a returning process of a converged state of optimization convergence calculation.

FIG. 7 is a flowchart of a process procedure until the controller 27 in the position detecting device 23 according to the second embodiment completes a returning process to a converged state of the optimization convergence calculation. As shown in FIG. 7, the controller 27 updates the respective field-strength detection values to be used for the optimization convergence calculation as at Steps S301 and S302 (see FIG. 4) (Step S401). When the predetermined time has not passed yet (NO at Step S402), the controller 27 repeats Steps S401 and S402 to thereby suspend the arithmetic processing of the position calculator 13 such as optimization convergence calculation for a predetermined time.

When the predetermined time passes (YES at Step S402), the controller 27 reads the final convergence result of the position calculator 13 from the convergence result information 15a in the storage unit 15 as at Steps S303 and S304 (see FIG. 4) (Step S403). The controller 27 then transmits the read final convergence result and the field-strength detection values of the respective detection coils 12 updated at Step S401 to the position calculator 13, and causes the position calculator 13 to perform the optimization convergence calculation using the field-strength detection values of the respective detection coils 12 and the final convergence result (the vector p representing the final convergence point) (Step S404). The controller 27 determines whether the result of the optimization convergence calculation performed by the position calculator 13 converges in the determination area as at Step S305 (see FIG. 4) (Step S405).

When a result of the one optimization convergence calculation performed by the position calculator 13 at Step S404 has not converged in the determination area (NO at Step S405), the controller 27 controls the coil selector 25 to switch one or more drive coils that generate the magnetic field in the drive coil group 24 (Step S406). At Step S406, the coil selector 25 switches one or more drive coils in the drive coil group 24 according to a predetermined sequence under control of the controller 27 to thereby sequentially apply the magnetic field to the LC marker 2c in the capsule endoscope 2 in different magnetization directions. In this case, the drive coil group 24 to be switched by the coil selector 25 sequentially applies, for example, the magnetic fields in the X-axis direction, Y-axis direction, and Z-axis direction of the absolute coordinate system to the LC marker 2c.

The controller 27 newly acquires the field-strength detection values $Bd_1, \ldots, Bd_n$ of the induced magnetic field emitted by the LC marker 2c due to the action of the magnetic field of one or more drive coils selected by the coil selector 25 at Step S406, to update the field-strength detection values of the respective detection coils to be used for the optimization convergence calculation (Step S407). The controller 27 returns to Step S404 to repeat the process procedure at Step S404 and subsequent steps.

When the result of the one optimization convergence calculation performed by the position calculator 13 at Step S404 converges in the determination area (YES at Step S405), it means that the diverged state of the optimization convergence calculation performed by the position calculator 13 is returned to a converged state, and the controller 27 returns to Step S113.

In the second embodiment of the present invention, as described above, the magnetic field is applied to an LC marker incorporated in a detection target such as a capsule endoscope by one or more drive coils selected in the drive coil group, thereby generating the induced magnetic field from the LC marker. The generated induced magnetic field is detected by the detection coils, and the arithmetic processor performs the optimization convergence calculation based on the evaluation function expressing an error between the measurement values (detection values) in the respective magnetic-field detection results acquired by the detection coils and the theoretical values. When the error value in the optimization convergence calculation diverges, one or more drive coils to apply the magnetic field to the LC marker is sequentially switched in the drive coil group to sequentially apply the magnetic field in different directions to the LC marker, and reacquires the field-strength detection value of the guiding magnetic field from the LC marker. The arithmetic processor restarts the optimization convergence calculation using the final convergence result acquired by the optimization convergence calculation as the starting point of calculation. Other features of the seconded embodiment are the same as those of the first embodiment. Accordingly, the second embodiment can achieve the same operational effects as those of the first embodiment, and the converged state of the optimization convergence calculation can be easily maintained or returned even when the detection target performs a sudden direction change.

Because the magnetic field is applied to the LC marker incorporated in the detection target to generate the induced magnetic field from the LC marker, power consumption of the detection target (for example, a medical device such as a capsule endoscope) can be reduced.

Third Embodiment

A third embodiment of the present invention is explained next. In the second embodiment, the induced magnetic field of the LC marker 2c incorporated in the capsule endoscope 2 as a detection target is detected by the detection coils 12. In the third embodiment, a detection coil that detects a magnetic field is incorporated in a capsule endoscope as a detection target, and the magnetic field generated by the drive coil group arranged outside the detection target is detected by the detection coil in the detection target, to acquire a magnetic-field detection result of the detection coil via the receiving device of the image signal.

Figure 8:
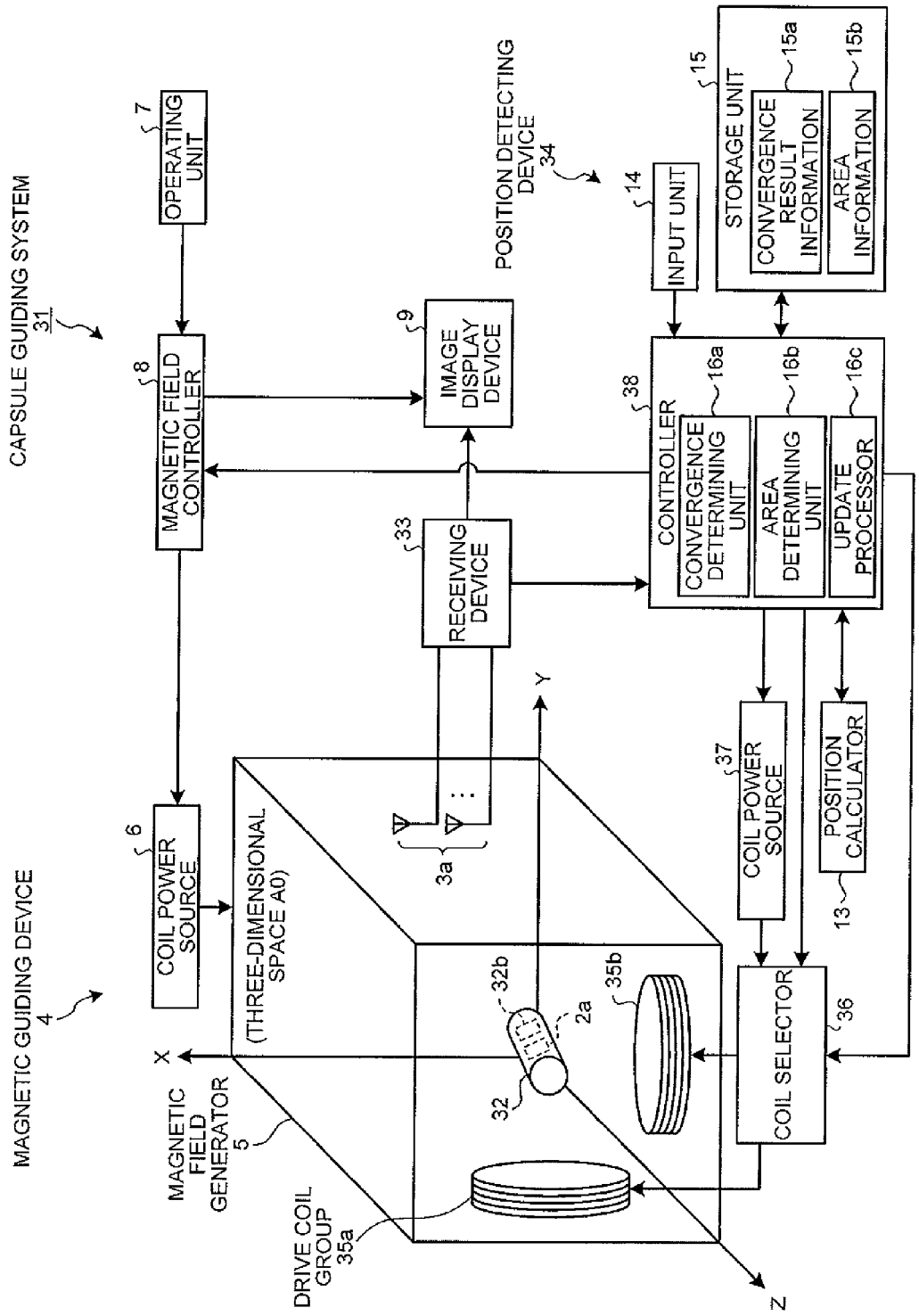
FIG. 8 is a schematic block diagram of a configuration example of a capsule guiding system according to a third embodiment of the present invention.

FIG. 8 is a schematic block diagram of a configuration example of a capsule guiding system according to the third embodiment of the present invention. As shown in FIG. 8, a capsule guiding system 31 according to the third embodiment includes a capsule endoscope 32 instead of the capsule endoscope 22, a receiving device 33 instead of the receiving device 3, and a position detecting device 34 instead of the position detecting device 23 in the capsule guiding system 21 according to the second embodiment. The capsule endoscope 32 includes a detection coil 32b instead of the LC marker 2c to wirelessly transmit a field-strength detection value of the detection coil 32b and in-vivo images of a subject to the receiving device 33. The position detecting device 34 includes drive coil groups 35a and 35b instead of the drive coil group 24, a coil selector 36 instead of the coil selector 25, a coil power source 37 instead of the coil power source 26, and a controller 38 instead of the controller 27 in the position detecting device 23. The position detecting device 34 does not include the magnetic field detector 11. The position detecting device 34 acquires the field-strength detection value from the receiving device 33. Other configurations of the third embodiment are the same as those of the second embodiment, and like components are denoted by like reference numerals.

The capsule endoscope 32 includes an imaging function and a wireless communication function in a capsule-shaped casing as in the capsule endoscope 22 according to the second embodiment, and is introduced into the organs of a subject to sequentially capture in-vivo images of the subject by using the imaging function. The capsule endoscope 32 includes the detection coil 32b instead of the LC marker 2c in the capsule-shaped casing. The detection coil 32b sequentially detects a plurality of magnetic fields generated by a plurality of drive coils of the external drive coil groups 35a and 35b. The capsule endoscope 32 wirelessly transmits the in-vivo images of the subject captured by the imaging function and the field-strength detection values $Bd_1, \ldots, Bd_n$ of the respective magnetic fields detected by the detection coil 32b. The field-strength detection values $Bd_1, \ldots, Bd_n$ detected by the detection coil 32b are an example of the magnetic field information of the detection target and are acquired by the controller 38 via the receiving device 33.

The receiving device 33 receives an in-vivo image group of a subject and the field-strength detection values $Bd_1, \ldots, Bd_n$ acquired by the detection coil 32b wirelessly transmitted by the capsule endoscope 32. Specifically, the receiving device 33 receives a radio signal from the capsule endoscope 32 via a plurality of the receiving antennas 3a, and performs a predetermined demodulation process with respect to the received radio signal to extract the in-vivo images and the field-strength detection values $Bd_i$ (i is an integer of 1 to n) included in the radio signal. The receiving device 33 sequentially transmits image signals of the acquired in-vivo images to the image display device 9, and sequentially transmits field strength signals indicating the acquired field-strength detection values $Bd_1$ to the controller 38. As a result, the receiving device 33 transmits the in-vivo image group of the subject captured by the capsule endoscope 32 to the image display device 9, and also transmits the field-strength detection values $Bd_1, \ldots, Bd_n$ acquired by the detection coil 32b in the capsule endoscope 32 to the controller 38.

The drive coil groups 35a and 35b are realized by a plurality of drive coils that generates the magnetic field for detecting the position and direction information of the capsule endoscope 32 in a subject. The drive coil groups 35a and 35b form a plurality of magnetic fields to be applied to the capsule endoscope 32 in the three-dimensional space A0. The magnetic fields generated by the drive coil groups 35a and 35b are sequentially detected by the detection coil 32b in the capsule endoscope 32. The field-strength detection results acquired by the detection coil 32b are used for calculation of the position and direction information of the capsule endoscope 32 in the three-dimensional space A0 (specifically, six variables in total of the position coordinate rc (x, y, z) of the capsule endoscope 32 and the magnetic dipole moment M (mx, my, mz)). Accordingly, it is desired that the number of drive coils to be arranged included in the drive coil groups 35a and 35b that sequentially apply the magnetic field to the detection coil 32b is six or more with respect to one detection coil 32b, and it is more desirable that the number of drive coils to be arranged is seven or more, taking switching of the drive coil groups into consideration.

The coil selector 36 functions as a switching unit of the drive coils, and selects a combination of a plurality of (for example, six or more) drive coils that generate the magnetic field from the drive coil groups 35a and 35b under control of the controller 38. The drive coils selected by the coil selector 36 generate a plurality of magnetic fields having strength and direction appropriate as the magnetic field penetrating the detection coil 32b in the coil axis direction, at the current position of the capsule endoscope 32 in the three-dimensional space A0.

The coil power source 37 has a plurality of power sources corresponding to the number of drive coils included in the drive coil groups 35a and 35b, and supplies the alternating current to the drive coils selected in the drive coil groups 35a and 35b by the coil selector 36 under control of the controller 38. In this case, the alternating signal generated by the coil power source 37 is applied to the selected plurality of (for example, six or more) drive coils of the drive coil groups 35a and 35b via the coil selector 36 to generate the magnetic fields in the drive coils.

The controller 38 controls the drive coil groups 35a and 35b, the coil selector 36, and the coil power source 37. Specifically, the controller 38 causes the coil selector 36 to select a plurality of drive coils in the drive coil groups 35a and 35b, and controls an energization amount of the coil power source 37 with respect to the drive coils (for example, six or more) selected by the coil selector 36 to thereby control a magnetic-field generation operation of the drive coil groups 35a and 35b through control of the energization amount. The controller 38 acquires the field-strength detection values $Bd_1, \ldots, Bd_n$ of a plurality of magnetic fields acquired by the detection coil 32b in the capsule endoscope 32 via the receiving device 33. The controller 38 calculates the field-strength theoretical values $B_1, \ldots, B_n$ of the magnetic fields based on the equation (1), and causes the position calculator 13 to perform the optimization convergence calculation based on the evaluation function (see the equation (2)) expressing an error between the field-strength detection values $Bd_1, \ldots, Bd_n$ and the field-strength theoretical values $B_1, \ldots, B_n$ of the magnetic fields. Further, the controller 38 controls the switching operation of the coil selector 36 for sequentially switching a combination of the plurality of (for example, six or more) drive coils from the drive coil groups 35a and 35b, in addition to the control for suspending the arithmetic processing of the position calculator 13 until a predetermined time passes, in the returning process of returning the diverged state of the optimization convergence calculation to a converged state. Other functions of the controller 38 are the same as those of the controller 27 in the position detecting device 23 according to the second embodiment.

When the position detecting device 34 that includes the controller 38 detects the position and direction information of the capsule endoscope 32 in a subject, the controller 38 repeatedly performs the process procedure substantially the same as that of the controller 27 in the position detecting device 23 according to the second embodiment. In this case, the controller 38 controls the coil selector 36 to sequentially switch a combination of the plurality of (for example, six or more) drive coils in the drive coil groups 35a and 35b at Step S406.

In the third embodiment of the present invention, as described above, a detection coil that detects the magnetic field is incorporated in a detection target such as a capsule endoscope. A plurality of magnetic fields formed by the plurality of drive coils selected in the drive coils group outside the detection target is applied to the detection target to detect the magnetic fields by the detection coil in the detection target, and magnetic-field detection results of the detection coil are sequentially acquired via the receiving device that receives the in-vivo images of a subject. The arithmetic processor performs the optimization convergence calculation based on the evaluation function expressing an error between the acquired measurement values (detection values) in the respective magnetic-field detection results and the theoretical values. When the error value in the optimization convergence calculation diverges, the combination of the drive coils that generate the magnetic fields is sequentially switched in the drive coil group to reacquire the respective field-strength detection values of the detection coil in the subject. The arithmetic processor restarts the optimization convergence calculation by using the final convergence result acquired by the previous optimization convergence calculation as the starting point of calculation. Other processes of the third embodiment are the same as those in the second embodiment. Accordingly, the third embodiment can achieve the same operational effects as those in the second embodiment, and the converged state of the optimization convergence calculation can be gained more easily.

Fourth Embodiment

A fourth embodiment of the present invention is explained next. In the first embodiment, the optimization convergence calculation is performed by the position calculator 13 every time the field-strength detection values $Bd_1, \ldots, Bd_n$ of the respective detection coils 12 are acquired from the magnetic field detector 11. In the fourth embodiment, one of the acquired field-strength detection values $Bd_1, \ldots, Bd_n$ is compared with a set threshold every time the field-strength detection values $Bd_1, \ldots, Bd_n$ of the respective detection coils 12 are acquired, and execution of the optimization convergence calculation is permitted or prohibited depending on a comparison result.

Figure 9:
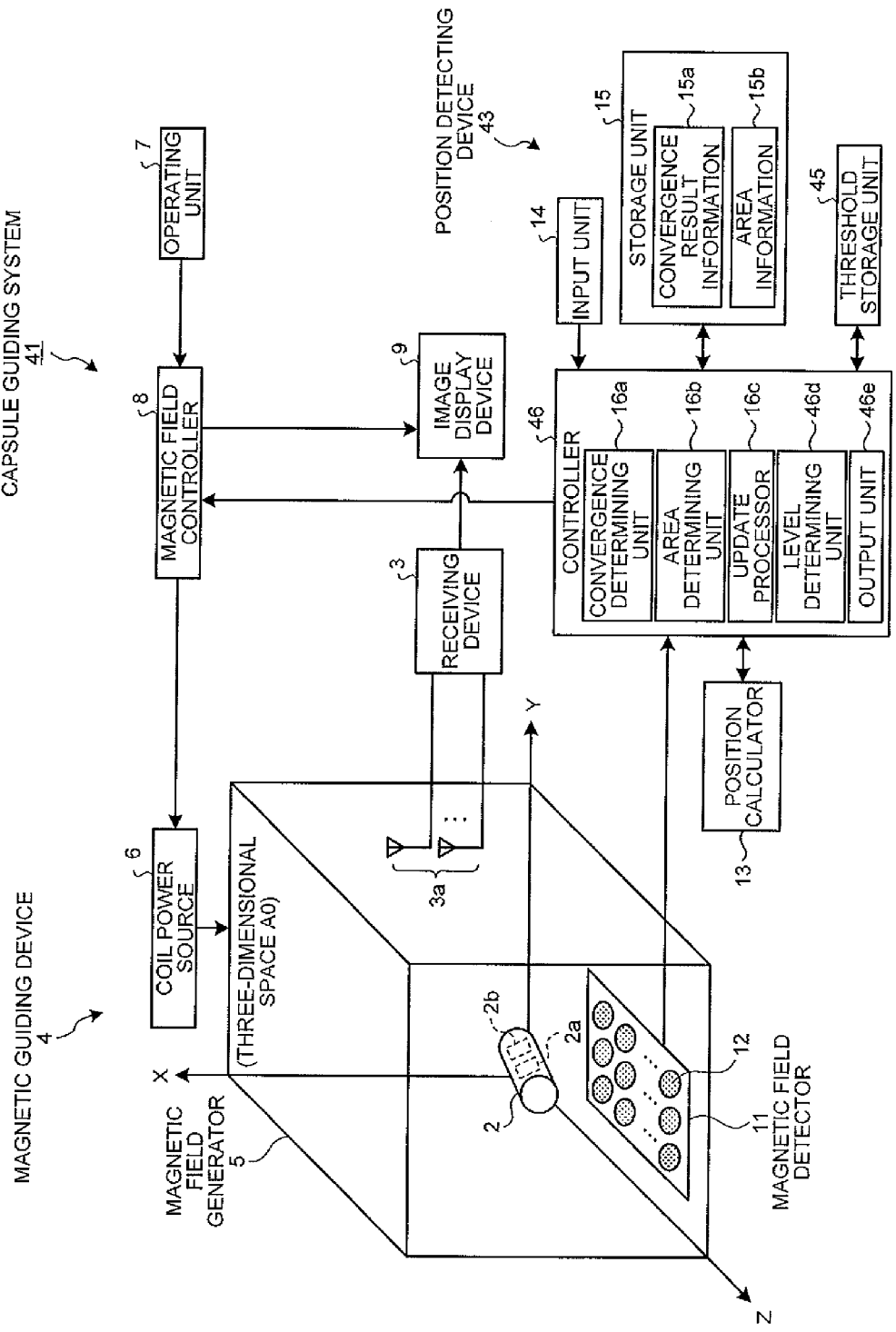
FIG. 9 is a schematic block diagram of a configuration example of a capsule guiding system according to a fourth embodiment of the present invention.

FIG. 9 is a schematic block diagram of a configuration example of a capsule guiding system according to the fourth embodiment of the present invention. As shown in FIG. 9, a capsule guiding system 41 according to the fourth embodiment includes a position detecting device 43 instead of the position detecting device 10 in the capsule guiding system 1 according to the first embodiment. The position detecting device 43 includes a controller 46 instead of the controller 16 in the position detecting device 10 according to the first embodiment, and also includes a threshold storage unit 45. Other configurations of the fourth embodiment are the same as those of the second embodiment, and like components are denoted by like reference numerals.

The threshold storage unit 45 stores a threshold relating to the magnetic field information of the capsule endoscope 2. Specifically, the threshold storage unit 45 stores a threshold relating to the field-strength measurement value of the magnetic field from the capsule endoscope 2 (more specifically, an alternating magnetic field from the magnetic field generator 2b) detected by the detection coils 12 in the magnetic field detector 11, that is, the respective field-strength detection values $Bd_1, \ldots, Bd_n$.

The threshold stored in the threshold storage unit 45 is calculated based on the field-strength measurement values by the respective detection coils in the magnetic field detector 11 at the time of arranging the magnetic field generator at the respective coordinate positions in the three-dimensional space A0. For example, a mesh is set with equal intervals in the three-dimensional space A0, and the magnetic field generator is arranged at respective points on the mesh. In this case, the direction of the magnetic field generator at the respective points can be set in a predetermined direction such as a predetermined vector direction represented by a vector component (1, 1, 1) in an XYZ coordinate system or respective directions specified when an XY plane, a YZ plane, and a ZX plane are rotated by a 45-degree pitch, or can be one finely assuming a plurality of directions. When the magnetic field generators are sequentially arranged at each point and in each direction, the magnetic field detector 11 detects the field strength by the detection coils 12 by position and direction of the magnetic field generator. That is, the magnetic field detector 11 acquires the field-strength detection values for the number of detection coils 12 for each magnetic field generator in an arbitrary position and direction in the three-dimensional space A0. The maximum value of the acquired field-strength detection values is sequentially recorded for each position and direction of the magnetic field generator. The minimum value is selected from the respective maximum values recorded for each position and direction of the magnetic field generator. Because the selected minimum value is the field strength of the magnetic field generator, it varies depending on a diameter or number of turns of the coil or a circuit to be connected. Therefore, the minimum value is multiplied by a coefficient relating to the diameter of the coil, the number of turns of the coil, and the circuit to be connected unique to the magnetic field generator $2b$ in the capsule endoscope 2. Accordingly, the minimum value is converted to the field-strength detection value corresponding to the magnetic field generator $2b$. The converted field-strength detection value is stored in the threshold storage unit 45 as the threshold relating to the magnetic field information of the capsule endoscope 2.

The controller 46 has a control function for controlling an information writing operation and an information reading operation of the threshold storage unit 45 in addition to the control function of the controller 16 in the position detecting device 10 according to the first embodiment. The controller 46 includes the convergence determining unit 16a, the area determining unit 16b, and the update processor 16c, and also includes a level determining unit 46d and an output unit 46e. The controller 46 compares the measurement value of the magnetic field information of the capsule endoscope 2 in the three-dimensional space A0 with the threshold in the threshold storage unit 45 to determine a difference between the measurement value of the magnetic field information and the threshold, and controls the optimization convergence calculation by the position calculator 13 based on a determination result. Specifically, when the measurement value of the magnetic field information is equal to or larger than the threshold, the controller 46 permits the optimization convergence calculation by the position calculator 13. When the measurement value of the magnetic field information is smaller than the threshold, the controller 46 prohibits the optimization convergence calculation by the position calculator 13. Other functions included in the controller 46 are the same as those of the controller 16 in the position detecting device 10 according to the first embodiment.

The level determining unit 46d determines whether the measurement value of the magnetic field information related to the capsule endoscope 2 in the three-dimensional space A0 is smaller than the threshold in the threshold storage unit 45. Specifically, every time the level determining unit 46d acquires the field-strength detection values $Bd_1, \ldots, Bd_n$ acquired by the respective detection coils 12 from the magnetic field detector 11, the level determining unit 46d reads the threshold from the threshold storage unit 45. The level determining unit 46d compares the maximum value of the field-strength detection values $Bd_1, \ldots, Bd_n$ with the threshold to determine whether the maximum value is smaller than the threshold.

The output unit 46e outputs a control signal for suspending the optimization convergence calculation to the position calculator 13. Specifically, when the level determining unit 46d determines that the measurement value of the magnetic field information related to the capsule endoscope 2 (that is, field-strength detection values $Bd_1, \ldots, Bd_n$) is smaller than the threshold, the output unit 46e outputs the control signal for suspending the optimization convergence calculation to the position calculator 13 based on a determination result.

Figure 10:
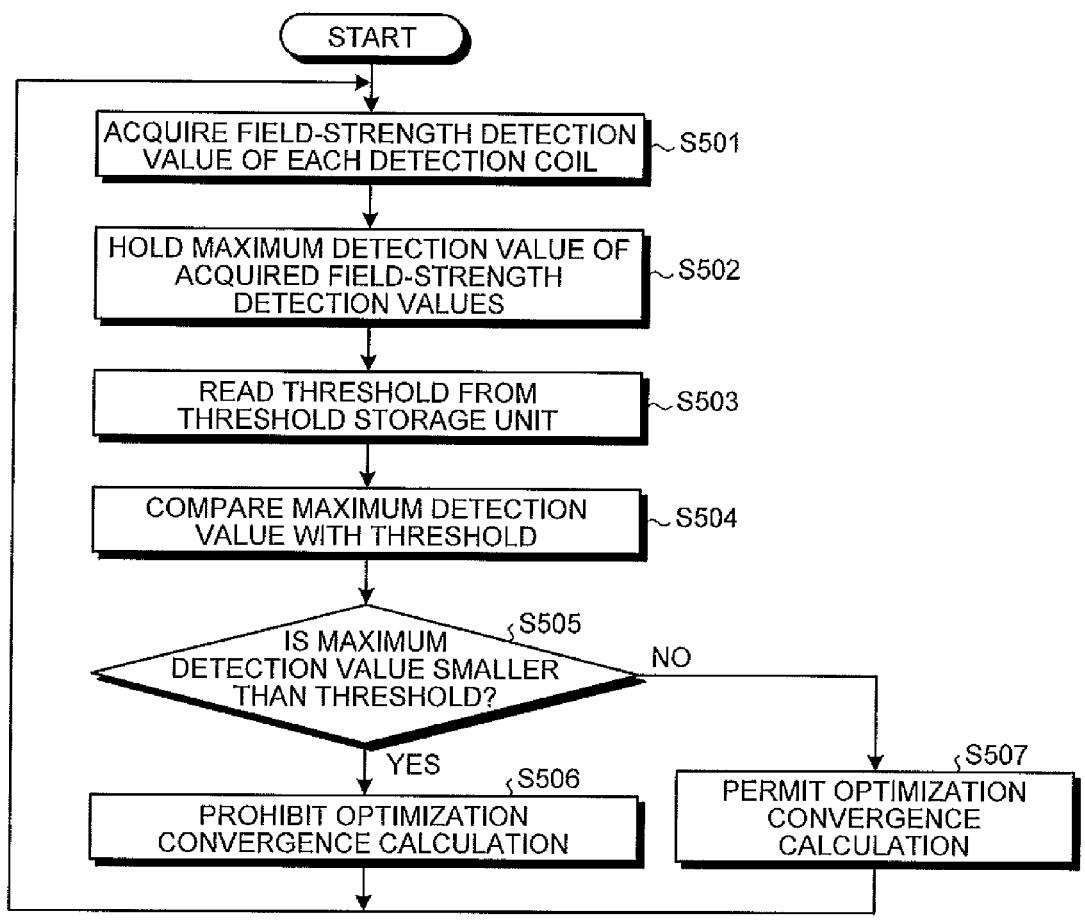
FIG. 10 is a flowchart exemplifying a process procedure performed by a position detecting device when optimization convergence calculation is permitted or prohibited according to a comparison result between a field-strength detection value and a threshold.

An operation of the position detecting device 43 according to the fourth embodiment of the present invention is explained next. FIG. 10 is a flowchart exemplifying a process procedure performed by the position detecting device when the optimization convergence calculation is permitted or prohibited depending on a comparison result between the field-strength detection value and the threshold. The operation of the position detecting device 43 according to the fourth embodiment is the same as that of the position detecting device 10 according to the first embodiment, except for the operation at the time of permitting or prohibiting the optimization convergence calculation depending on the comparison result between the field-strength detection value and the threshold. The operation of the position detecting device 43 at the time of permitting or prohibiting the optimization convergence calculation by the position calculator 13 depending on the comparison result between the field-strength detection values $Bd_1, \ldots, Bd_n$ acquired by the respective detection coils 12 and the preset threshold is explained below with reference to FIG. 10.

As shown in FIG. 10, the controller 46 in the position detecting device 43 according to the fourth embodiment acquires the field-strength detection values $Bd_1, \ldots, Bd_n$ of the respective detection coils 12 from the magnetic field detector 11 (Step S501) in the same manner as at Step S103, and holds the maximum detection value, which is the maximum value of the acquired field-strength detection values $Bd_1, \ldots, Bd_n$ (Step S502). In this case, the level determining unit 46d acquires and holds the maximum detection value of the acquired field-strength detection values $Bd_1, \ldots, Bd_n$, every time the field-strength detection values $Bd_1, \ldots, Bd_n$ of the respective detection values 12 are acquired from the magnetic field detector 11.

The controller 46 then reads the threshold from the threshold storage unit 45 (Step S503), and compares the read threshold with the maximum detection value held at Step S502 (Step S504) to determine a difference between the maximum detection value and the threshold (Step S505). In this case, the level determining unit 46d reads the threshold from the threshold storage unit 45, which is stored in the threshold storage unit 45 beforehand as the threshold of the measurement value of the magnetic field information related to the capsule endoscope 2. Subsequently, the level determining unit 46d compares the read threshold with the maximum detection value held at Step S502, to determine whether the maximum detection value is smaller than the threshold.

When having determined that the maximum detection value is smaller than the threshold at Step S505 (YES at Step S505), the controller 46 prohibits the optimization convergence calculation by the position calculator 13 (Step S506), and then returns to Step S501 to repeat the process procedure at Step S501 and subsequent steps.

At Steps S505 and S506, the level determining unit 46d determines that the maximum detection value of the field-strength detection values $Bd_1, \ldots, Bd_n$ is smaller than the threshold as a result of a comparing process at Step S504. The output unit 46e generates a control signal for prohibiting execution of the optimization convergence calculation based on a determination result of the level determining unit 46d, and outputs the generated control signal to the position calculator 13.

The threshold in the threshold storage unit 45 indicates the smallest value of the respective maximum values of the magnetic-field detection values detectable by position and direction in the three-dimensional space A0. Accordingly, when the maximum detection value of the field-strength detection values $Bd_1, \ldots, Bd_n$ acquired by the respective detection coils is smaller than the threshold, there is high possibility that the current position of the capsule endoscope 2 as a detection target is outside the three-dimensional space A0, at least outside the detection space of the position detecting device 43. Based on this fact, when the maximum detection value is smaller than the threshold, the level determining unit 46d determines that the current state is not suitable for performing position calculation of the capsule endoscope 2, and the output unit 46e outputs a control signal for prohibiting execution of the optimization convergence calculation to the position calculator 13.

Upon reception of the control signal for prohibiting the execution, the position calculator 13 suspends the optimization convergence calculation at Step S106 shown in FIG. 2. As a result, the position calculator 13 does not need to perform useless optimization convergence calculations having high possibility of reaching the diverged state, in a state with the capsule endoscope 2 as a detection target being not present in the three-dimensional space A0 (not present at least in the detection space of the position detecting device 43).

In practice, the level of an acquisition signal of the field-strength detection values $Bd_1, \ldots, Bd_n$ can drift due to a peripheral temperature or the like of the capsule endoscope 2. Therefore, it is desired that the threshold prestored in the threshold storage unit 45 is set to a value slightly larger than a calculated value, taking the drift of the signal level of the field-strength detection values $Bd_1, \ldots, Bd_n$ into consideration.

When having determined that the maximum detection value is not smaller than the threshold, that is, equal to or larger than the threshold at Step S505 (NO at Step S505), the controller 46 permits the optimization convergence calculation by the position calculator 13 (Step S507), and returns to Step S501 to repeat the process procedure at Step S501 and subsequent steps.

At Steps S505 and S506, the level determining unit 46d determines that the maximum detection value of the field-strength detection values $Bd_1, \ldots, Bd_n$ is equal to or larger than the threshold as a result of comparison at Step S504. In this case, the output unit 46e does not output the control signal mentioned above for prohibiting the execution to the position calculator 13. As a result, the position calculator 13 is allowed to perform the optimization convergence calculation, and starts or continues the optimization convergence calculation at Step S104 shown in FIG. 2.

The controller 46 can perform the process procedure at Steps S501 to S507 concurrently with the process procedure at Steps S103 to S106 shown in FIG. 2. Alternatively, the controller 46 can perform the process procedure at Steps S501 to S505 after performing Step S102 can repeat the process procedure at Step S104 and subsequent steps after performing Step S506 or can repeat the process procedure at Step S102 and subsequent steps, after performing Step S507.

Figure 11:
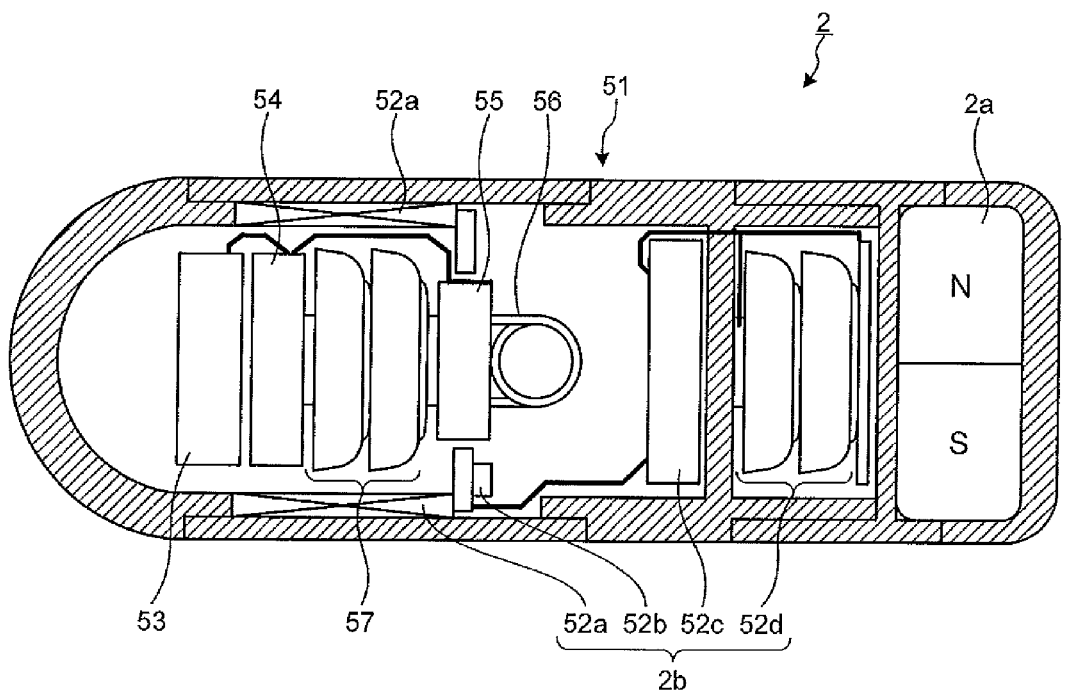
FIG. 11 is a schematic diagram of a configuration example of a capsule endoscope as a detection target.
Figure 12:
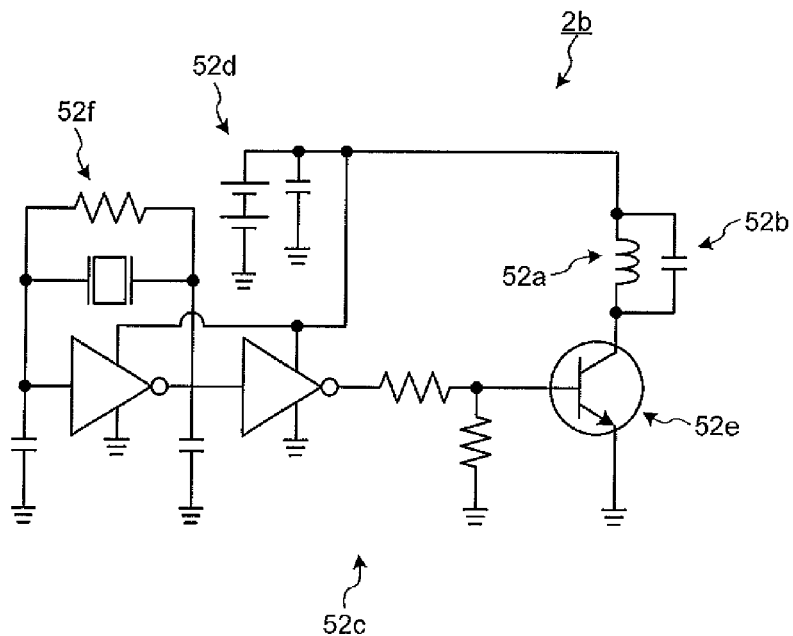
FIG. 12 is a schematic diagram of an example of a circuit configuration of a magnetic field generator incorporated in a capsule endoscope.

A configuration of the capsule endoscope 2 as a detection target is explained next in detail. FIG. 11 is a schematic diagram of a configuration example of a capsule endoscope as a detection target. FIG. 12 is a schematic diagram of an example of a circuit configuration of a magnetic field generator incorporated in the capsule endoscope. An internal configuration of the capsule endoscope 2 is shown in FIG. 12.

As shown in FIG. 11, the capsule endoscope 2 includes a capsule-shaped casing 51 having a size introducible into organs of a subject such as a patient, and includes the magnet 2a and the magnetic field generator 2b in the capsule-shaped casing 51. The capsule endoscope 2 also includes an imaging unit 53, a signal processor 54, a wireless transmitter 55, an antenna coil 56, and an endoscope battery 57 in the capsule-shaped casing 51.

The imaging unit 53 is realized by using a light emitting unit such as an LED, a solid-state imaging element such as a CCD, and an optical system such as a condenser lens. The imaging unit 53 illuminates a subject through an optical dome of the capsule-shaped casing 51 and receives reflecting light from the illuminated subject to capture images of the subject (for example, in-vivo images of the subject).

The signal processor 54 acquires the image captured by the imaging unit 53, and performs predetermined signal processing with respect to the acquired signal to generate an image signal including image data by the imaging unit 53. The wireless transmitter 55 performs a predetermined communication process such as a modulation process on the image signal generated by the signal processor 54 to generate the radio signal including the image signal. The wireless transmitter 55 is connected to the antenna coil 56, and transmits the generated radio signal to an external receiving device (not shown) via the antenna coil 56.

The endoscope battery 57 is, for example, a button-shaped battery, and supplies driving power to the imaging unit 53, the signal processor 54, and the wireless transmitter 55. The endoscope battery 57 needs only to supply the power required for the imaging unit 53, the signal processor 54, and the wireless transmitter 55 for a predetermined time or longer, and the number of endoscope batteries to be arranged is not particularly limited to two, and can be one or more.

As described above, the magnet 2a is an element to realize magnetic guidance of the capsule endoscope 2 by the magnetic guiding device 4, and as shown in FIG. 11, is arranged at a rear end of the capsule-shaped casing 51. Accordingly, the magnet 2a is arranged away from the antenna coil 56 as much as possible. As a result, deterioration of antenna characteristics of the antenna coil 56 is prevented. The magnet 2a is arranged such that a magnetization direction thereof is vertical to an opening direction of the antenna coil 56 to minimize such an occasion that the magnetic field generated by the magnet 2a passes the antenna coil 56. A partition, which is a part of the capsule-shaped casing 51, is provided between the magnet 2a and a battery dedicated to the magnetic field generator 2b (a battery 52d for a magnetic field generator) to maintain a predetermined gap therebetween. This is because a magnetic force of the magnet 2a is weakened by a magnetic body of the battery 52d for a magnetic field generator, thereby preventing a force acting on the capsule endoscope 2 from decreasing at the time of magnetic guidance. The rear end of the capsule-shaped casing 51 incorporating the magnet 2a is detachable so that the magnet 2a can be easily incorporated therein or detached therefrom.

The magnetic field generator 2b generates the magnetic field used for detecting the position and direction of the capsule endoscope 2, and as shown in FIGS. 11 and 12, includes a resonance coil 52a, a resonance capacitor 52b, an oscillation driving circuit 52c, and the battery 52d for a magnetic field generator.

The battery 52d for a magnetic field generator is a single-purpose battery for the magnetic field generator 2b, and is realized by, for example, a button-shaped battery. The battery 52d for a magnetic field generator is arranged away from the antenna coil 56 as much as possible, thereby preventing deterioration of the antenna characteristics of the antenna coil 56. Further, a part of the battery 52d for a magnetic field generator, which is incorporated in the capsule-shaped casing 51, is detachable so that the battery 52d for a magnetic field generator can be easily replaced. The power generated by the battery 52d for a magnetic field generator is supplied to the oscillation driving circuit 52c.

The oscillation driving circuit 52c is configured by using a switching element 52e and a crystal resonance circuit 52f as shown in FIG. 12. When the power is supplied by the battery 52d for a magnetic field generator, the oscillation driving circuit 52c generates a signal by the crystal resonance circuit 52f, and outputs the generated signal to the resonance coil 52a and the resonance capacitor 52b via the switching element 52e.

The resonance coil 52a and the resonance capacitor 52b form the resonance circuit as shown in FIG. 12, and generates the magnetic field upon reception of the signal from the oscillation driving circuit 52c. The magnetic field generated by the resonance coil 52a and the resonance capacitor 52b is output outside of the capsule endoscope 2, and then detected by the magnetic field detector 11.

The battery 52d for a magnetic field generator needs only to supply power required for generating the magnetic field by the resonance coil 52a and the resonance capacitor 52b for a predetermined time or longer, and the number of batteries to be arranged is not particularly limited to two, and can be one or more. The magnetic field generator 2b can share the power of the endoscope battery 57, and in this case, the battery 57 for a magnetic field generator does not need to be provided.

In the fourth embodiment of the present invention, as described above, the threshold of the measurement value of the magnetic field information related to the capsule endoscope in the three-dimensional space is stored beforehand in the threshold storage unit, and every time the magnetic field detector detects the strength of the magnetic field from the capsule endoscope, the field-strength detection value acquired by the magnetic field detector is compared with the threshold in the threshold storage unit to determine a difference between the field-strength detection value and the threshold. When the field-strength detection value is smaller than the threshold, the optimization convergence calculation by the position calculator is prohibited. When the field-strength detection value is equal to or larger than the threshold, the optimization convergence calculation by the position calculator is permitted. Other features of the fourth embodiment are the same as those in the first embodiment. Accordingly, the fourth embodiment can achieve the same operational effect as those of the first embodiment, and the optimization convergence calculation by the position calculator can be suspended in a state where there is no capsule endoscope in a space capable of detecting the position, thereby enabling to realize a position detecting device capable of reducing the power of the device consumed to perform the optimization convergence calculation.

Further, in a state where there is no capsule endoscope in a space capable of detecting the position, the optimization convergence calculation by the position calculator is not performed. Therefore, it is possible to prevent a case that the position calculation of the capsule endoscope having a large error is performed and the error value in the optimization convergence calculation diverges. Accordingly, the starting point of calculation having a large error is not set at the time of performing the next optimization convergence calculation. As a result, it is possible to prevent a case that the error value is diffused erroneously at the time of performing the normal optimization convergence calculation after the error value has converged.

In the third embodiment of the present invention described above, one detection coil 32b is incorporated in the capsule endoscope 32. However, a plurality of detection coils can be incorporated in the capsule endoscope 32. In this case, it is desired that a product of the number of drive coils to be arranged, which are included in the drive coil groups 35a and 35b that apply a plurality of magnetic fields to the plurality of detection coils, and the number of detection coils to be arranged is six or more.

In the first to fourth embodiments of the present invention described above, the position detecting device incorporated in the capsule guiding system that magnetically guides the capsule endoscope introduced into a subject to detect the position information of the capsule endoscope in the subject is exemplified. However, the position detecting device according to the present invention needs only to detect the position information by performing the optimization convergence calculation based on the evaluation function expressing an error between the measurement value and the theoretical value of the magnetic field information of a detection target, and is not particularly limited to the position detecting device combined with the capsule guiding system.

The detection target whose position information is detected by the position detecting device according to the present invention is not limited to a medical device such as the capsule endoscope described above. Further, the capsule medical device whose position information is detected as a detection target is not limited to the capsule endoscope, and can be a capsule pH-measuring device that measures pH in a living body, a capsule drug-administration device including a function of spraying or injecting a drug into a living body, or a capsule collecting device that collects a material in a living body.

In the second and third embodiments described above, the optimization convergence calculation by the position calculator 13 is performed every time the field-strength detection values $Bd_1, \ldots, Bd_n$ of the respective detection coils 12 are acquired from the magnetic field detector 11. However, as in the fourth embodiment, the maximum value of the acquired field-strength detection values $Bd_1, \ldots, Bd_n$ is compared with the set threshold, every time the field-strength detection values $Bd_1, \ldots, Bd_n$ of the respective detection coils 12 are acquired, to permit or prohibit the optimization convergence calculation according to a comparison result. That is, the position detecting devices 23 and 34 according to the second and third embodiments can also include the threshold storage unit 45, and the controllers 27 and 38 in the position detecting devices 23 and 34 can also include the level determining unit 46d and the output unit 46e.

In this case, the threshold storage unit 45 in the position detecting devices 23 and 34 according to the second and third embodiments stores a plurality of thresholds of the magnetic field information related to the capsule endoscope for each axial direction (an opening direction) of the magnetic-field generation coils included in the drive coil group. The controllers 27 and 38 select a threshold to be compared with the measurement value of the magnetic field information (that is, the maximum value of the field-strength detection values $Bd_1, \ldots, Bd_n$) from the plurality of thresholds in the threshold storage unit 45, corresponding to a magnetic-field generation coil, among the magnetic-field generation coils, that applies a magnetic field to the capsule endoscope.

In the controllers 27 and 38, the level determining unit 46d identifies the magnetic-field generation coil being driven from the drive coil group based on the control signal with respect to the coil selector, and selects a threshold corresponding to the identified magnetic-field generation coil from the plurality of thresholds in the threshold storage unit 45. The level determining unit 46d then reads the selected threshold from the threshold storage unit 45, and as in the fourth embodiment, compares the threshold with the maximum detection value of the field-strength detection values $Bd_1, \ldots, Bd_n$, to determine a difference between the maximum detection value and the threshold. As in the fourth embodiment, when the maximum detection value is smaller than the threshold, the output unit 46e needs only to output a control signal for prohibiting execution of calculation to the position calculator 13.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detecting device comprising:
   a position calculator that performs an optimization convergence calculation using an evaluation function that expresses an error between a measurement value and a theoretical value of magnetic field information of a detection target to calculate at least a position of the detection target as a convergence result;
   a storage unit that stores a final convergence result of the optimization convergence calculation performed by the position calculator, wherein the final convergence result is the latest convergence result in a time series; and
   a controller that
      determines whether a convergence result of the optimization convergence calculation converges,
      suspends the optimization convergence calculation performed by the position calculator when the convergence result does not converge, and
      performs, after a predetermined time has passed, a returning process of returning a state of the optimization convergence calculation to a converged state by causing the position calculator to perform the optimization convergence calculation based on the final convergence result.

2. The position detecting device according to claim 1, wherein the controller sets a determination area in a position detection space of the detection target to determine whether the position of the detection target is in the determination area, and performs the returning process when the position is outside the determination area, and
   the storage unit stores, when the result of the optimization convergence calculation converges and the position of the detection target is in the determination area, the final convergence result of the optimization convergence calculation.

3. The position detecting device according to claim 2, wherein the controller sets, in the determination area, an inside area smaller than the determination area by at least a space corresponding to a position variation range of the detection target, determines whether the position of the detection target is in the inside area, expands the determination area by at least the space corresponding to a variation range of the detection target when the position of the detection target is outside the inside area, determines whether the position of the detection target is in the expanded determination area, and performs the returning process when the position of the detection target is outside the expanded determination area.

4. The position detecting device according to claim 1, further comprising:
   a plurality of magnetic-field generation coils that are arranged around the detection target and apply a magnetic field to the detection target; and
   a switching unit that selects from the magnetic-field generation coils at least one magnetic-field generation coil for generating the magnetic field,
   wherein the detection target has a resonance circuit that resonates due to the magnetic field generated by the at least one magnetic-field generation coil to newly generate a resonance magnetic field, and
   the controller performs, when a result of the optimization convergence calculation in the returning process does not converge, the returning process again after causing the switching unit to switch the magnetic-field generation coils.

5. The position detecting device according to claim 2, further comprising:
   a plurality of magnetic-field generation coils that are arranged around the detection target and apply a magnetic field to the detection target; and
   a switching unit that selects from the magnetic-field generation coils at least one magnetic-field generation coil for generating the magnetic field,
   wherein the detection target has a resonance circuit that resonates due to the magnetic field generated by the at least one magnetic-field generation coil to newly generate a resonance magnetic field, and
   the controller performs, when the position of the detection target calculated by the optimization convergence calculation in the returning process is outside the determination area, the returning process again after causing the switching unit to switch the magnetic-field generation coils.

6. The position detecting device according to claim 3, further comprising:
   a plurality of magnetic-field generation coils that are arranged around the detection target and apply a magnetic field to the detection target; and
   a switching unit that selects from the magnetic-field generation coils at least one magnetic-field generation coil for generating the magnetic field,
   wherein the detection target has a resonance circuit that resonates due to the magnetic field generated by the at least one magnetic-field generation coil to newly generate a resonance magnetic field, and
   the controller performs, when the position of the detection target calculated by the optimization convergence calculation in the returning process is outside the expanded determination area, the returning process again after causing the switching unit to switch the magnetic-field generation coils.

7. The position detecting device according to claim 1, further comprising:
   a plurality of magnetic-field generation coils that are arranged around the detection target and apply a magnetic field to the detection target; and a switching unit that selects from the magnetic-field generation coils at least one magnetic-field generation coil for generating the magnetic field, wherein the detection target has a magnetic field detector that detects the magnetic field generated by the at least one magnetic-field generation coil as the magnetic field information, and the controller acquires the magnetic field information detected by the magnetic field detector, causes the position calculator to perform the optimization convergence calculation using the acquired magnetic field information, and performs, when a result of the optimization convergence calculation in the returning process does not converge, the returning process again after causing the switching unit to switch the magnetic-field generation coils.

8. The position detecting device according to claim 2, further comprising:

a plurality of magnetic-field generation coils that are arranged around the detection target and apply a magnetic field to the detection target; and a switching unit that selects from the magnetic-field generation coils at least one magnetic-field generation coil for generating the magnetic field, wherein the detection target has a magnetic field detector that detects the magnetic field generated by the at least one magnetic-field generation coil as the magnetic field information, and the controller acquires the magnetic field information detected by the magnetic field detector, causes the position calculator to perform the optimization convergence calculation using the acquired magnetic field information, and performs, when the position of the detection target calculated by the optimization convergence calculation in the returning process is outside the determination area, the returning process again after causing the switching unit to switch the magnetic-field generation coils.

9. The position detecting device according to claim 3, further comprising:

a plurality of magnetic-field generation coils that are arranged around the detection target and apply a magnetic field to the detection target; and a switching unit that selects from the magnetic-field generation coils at least one magnetic-field generation coil for generating the magnetic field, wherein the detection target has a magnetic field detector that detects the magnetic field generated by the at least one magnetic-field generation coil as the magnetic field information, and the controller acquires the magnetic field information detected by the magnetic field detector, causes the position calculator to perform the optimization convergence calculation using the acquired magnetic field information, and performs, when the position of the detection target calculated by the optimization convergence calculation in the returning process is outside the expanded determination area, the returning process again after causing the switching unit to switch the magnetic-field generation coils.

10. The position detecting device according to claim 1, wherein the controller comprises a convergence determining unit that determines whether a result of the optimization convergence calculation converges, and the controller suspends, when the convergence determining unit determines that the result of the optimization convergence calculation does not converge, the optimization convergence calculation performed by the position calculator, and performs the returning process after a predetermined time has passed.

11. The position detecting device according to claim 2, wherein the controller comprises an area determining unit that determines an area containing the position of the detection target calculated by the optimization convergence calculation, the area determining unit determines whether the position of the detection target is in the determination area, the controller performs, when the area determining unit determines that the position of the detection target is outside the determination area, the returning process, and the storage unit stores, when a result of the optimization convergence calculation converges and the area determining unit determines that the position of the detection target is in the determination area, the final convergence result of the optimization convergence calculation.

12. The position detecting device according to claim 11, wherein the controller sets, in the determination area, an inside area smaller than the determination area by at least a space corresponding to a position variation range of the detection target, the area determining unit determines whether the position of the detection target is in the inside area, the controller expands the determination area by at least the space corresponding to a variation range of the detection target when the area determining unit determines that the position of the detection target is outside the inside area, the area determining unit determines whether the position of the detection target is in the expanded determination area, and the controller performs the returning process when the area determining unit determines that the position of the detection target is outside the expanded determination area.

13. A position detecting device comprising:

a position calculator that performs an optimization convergence calculation using an evaluation function that expresses an error between a measurement value and a theoretical value of magnetic field information of a detection target to calculate at least a position of the detection target;

a threshold storage unit that stores a threshold concerning a measurement value of the magnetic field information; and a controller that compares the measurement value of the magnetic field information with the threshold to determine a difference between the measurement value of the magnetic field information and the threshold, permits, when the measurement value of the magnetic field information is equal to or larger than the threshold, the optimization convergence calculation performed by the position calculator, and prohibits, when the measurement value of the magnetic field information is smaller than the threshold, the optimization convergence calculation performed by the position calculator.

14. The position detecting device according to claim 13, wherein the controller comprises:

a level determining unit that determines whether the measurement value of the magnetic field information is smaller than the threshold; and an output unit that outputs to the position calculator, when the level determining unit determines that the measurement value of the magnetic field information is smaller than the threshold, a control signal for suspending the optimization convergence calculation performed by the position calculator.

15. The position detecting device according to claim 13, further comprising a magnetic field detector that detects using a plurality of magnetic-field detection coils a magnetic field generated by the detection target and outputs each of detection results acquired by the magnetic-field detection coils to the controller as the measurement value of the magnetic field information.

16. The position detecting device according to claim 15, wherein the measurement value of the magnetic field information is a maximum value of the detection results acquired by the magnetic-field detection coils.

17. The position detecting device according to claim 15, further comprising:
   a plurality of magnetic-field generation coils that are arranged around the detection target and apply a magnetic field to the detection target; and
   a switching unit that selects from the magnetic-field generation coils at least one magnetic-field generation coil for generating the magnetic field,
   wherein the detection target generates a resonance magnetic field upon reception of the magnetic field applied by the at least one magnetic-field generation coil, and
   the magnetic field detector detects using the magnetic-field detection coils the resonance magnetic field generated by the detection target and outputs each of detection results of the resonance magnetic field acquired by the magnetic-field generation coils to the controller as the measurement values of the magnetic field information.

18. The position detecting device according to claim 17, wherein the threshold storage unit stores a plurality of thresholds concerning the measurement values of the magnetic field information for each axial direction of the magnetic-field generation coils, and
   the controller selects from the thresholds a threshold to be compared with the measurement value of the magnetic field information, the threshold corresponding to the magnetic-field generation coil, among the magnetic-field generation coils, that applies the magnetic field to the detection target.

* * * * *